(12) United States Patent
Shani et al.

(10) Patent No.: US 8,934,964 B2
(45) Date of Patent: Jan. 13, 2015

(54) ANALYSIS OF ELECTROCARDIOGRAM SIGNALS

(71) Applicant: Bio Signal Analysis Ltd., Ramat-Efal (IL)

(72) Inventors: Benjamin Shani, Ramat-HaSharon (IL); Shai Revzen, Haifa (IL); Aaron Frimerman, Tel-Aviv (IL)

(73) Assignee: Bio Signal Analysis Ltd., Ramat-Efal (IL)

( * ) Notice: Subject to any disclaimer, the term of this patent is extended or adjusted under 35 U.S.C. 154(b) by 0 days.

(21) Appl. No.: 14/088,402

(22) Filed: Nov. 24, 2013

(65) Prior Publication Data

US 2014/0081163 A1  Mar. 20, 2014

Related U.S. Application Data

(62) Division of application No. 11/920,577, filed as application No. PCT/IL2006/000576 on May 16, 2006, now Pat. No. 8,620,415.

(60) Provisional application No. 60/681,431, filed on May 17, 2005.

(51) Int. Cl.
  *A61B 5/04* (2006.01)
  *A61B 5/0456* (2006.01)
  *A61B 5/044* (2006.01)
  *A61B 5/0452* (2006.01)
  *A61B 5/0468* (2006.01)

(52) U.S. Cl.
  CPC .............. *A61B 5/044* (2013.01); *A61B 5/0456* (2013.01); *A61B 5/04011* (2013.01); *A61B 5/0452* (2013.01); *A61B 5/0468* (2013.01); *A61B 5/04017* (2013.01)
  USPC ............................ 600/516; 600/509; 600/521

(58) Field of Classification Search
  CPC .. A61B 5/0452; A61B 5/0402; A61B 5/0456; A61B 5/0472
  USPC .......................... 600/508–509, 516–518, 521
  See application file for complete search history.

(56) References Cited

U.S. PATENT DOCUMENTS

| 5,694,943 | A | 12/1997 | Brewer et al. |
| 6,169,919 | B1 | 1/2001 | Nearing et al. |
| 6,370,423 | B1 | 4/2002 | Guerrero et al. |

(Continued)

FOREIGN PATENT DOCUMENTS

| EP | 1050271 | 11/2000 |
| WO | WO 2005/008418 | 1/2005 |
| WO | WO 2006/123334 | 11/2006 |

OTHER PUBLICATIONS

Communication Pursuant to Article 94(3) EPC Dated Apr. 2, 2009 From the European Patent Office Re.: Application No. 06745102.1.

(Continued)

Primary Examiner — Catherine Voorhees

(57) ABSTRACT

A method for graphical representation of a train of ECG complexes having an R wave and a T-P interval and having variable isoelectric baselines. The method involves aligning the complexes in terms of signal amplitude by obtaining a baseline, thereby to provide a graphical representation of said train of ECG complexes; and aligning said complexes temporally using corresponding predetermined points.

8 Claims, 45 Drawing Sheets
(4 of 45 Drawing Sheet(s) Filed in Color)

(56) References Cited

U.S. PATENT DOCUMENTS

| | | |
|---|---|---|
| 6,668,189 B2 | 12/2003 | Kaiser et al. |
| 6,778,852 B2 | 8/2004 | Galen et al. |
| 7,079,888 B2 | 7/2006 | Oung et al. |
| 7,412,283 B2 | 8/2008 | Ginzburg et al. |
| 7,500,955 B2 | 3/2009 | Sweeney |
| 2003/0069512 A1 | 4/2003 | Kaiser et al. |
| 2004/0147981 A1 | 7/2004 | Bardy |
| 2004/0249294 A1* | 12/2004 | Thulasidas ............... 600/509 |
| 2006/0264769 A1* | 11/2006 | Satin et al. ............... 600/509 |
| 2007/0021679 A1 | 1/2007 | Narayan et al. |
| 2008/0194978 A1 | 8/2008 | Beker et al. |
| 2008/0299583 A1 | 12/2008 | Shain et al. |
| 2008/0319309 A1 | 12/2008 | Bredno et al. |
| 2009/0234239 A1 | 9/2009 | Shani et al. |

OTHER PUBLICATIONS

Communication Pursuant to Article 94(3) EPC Dated Nov. 10, 2011 From the European Patent Office Re.: Application No. 06745102.1.

Communication Relating to the Results of the Partial International Search Dated Sep. 29, 2006 From the International Searching Authority Re.: Application No. PCT/IL2006/000576.

International Preliminary Report on Patentability Dated Nov. 29, 2007 From the International Bureau of WIPO Re.: Application No. PCT/IL2006/000576.

International Search Report Dated Jan. 17, 2007 From the International Searching Authority Re.: Application No. PCT/IL2006/000576.

Notice of Allowance Dated Jul. 30, 2013 From the US Patent and Trademark Office Re. U.S. Appl. No. 11/920,577.

Official Action Dated Nov. 8, 2011 From the US Patent and Trademark Office Re. U.S. Appl. No. 11/920,577.

Official Action Dated Aug. 17, 2011 From the US Patent and Trademark Office Re. U.S. Appl. No. 11/920,577.

Official Action Dated Jun. 29, 2012 From the US Patent and Trademark Office Re. U.S. Appl. No. 11/920,577.

Response Dated Sep. 12, 2011 to Official Action of Aug. 17, 2011 From the US Patent and Trademark Office Re. U.S. Appl. No. 11/920,577.

Supplemental Notice of Allowability Dated Aug. 27, 2013 From the US Patent and Trademark Office Re. U.S. Appl. No. 11/920,577.

Written Opinion Dated Jan. 17, 2007 From the International Searching Authority Re.: Application No. PCT/IL2006/000576.

\* cited by examiner

Case 1: L. Y., Normal coronary arteries, Lt. artery

Case 1: L. Y., Normal coronary arteries, Rt. artery

Fig. 17  Case 1: L. Y.: Analysis result of normal ECG and normal coronary artery group (lead 2)

Fig. 18 Case 2: S. A., Normal Electrocardiogram

Case 2: S. A., Normal coronary arteries, Lt. artery

Case 2: S. A., Normal coronary arteries, Rt. artery

Fig. 21  Case 2: S. A., Analysis result of normal ECG and normal coronary artery group (lead 1)

Fig. 22  Case 3: Z. M., Normal Electrocardiogram

Case 3: Z. M., Coronary artery disease, Lt. artery

Fig. 24  Case 3: Z. M., Coronary artery disease, Lt. artery

Fig. 25  Case 3: Z. M., Coronary artery disease, Rt. artery

Fig. 26  Case 3: Z. M., Analysis result of normal ECG and diseased coronary artery group (lead 1)

Fig. 28 Case 4: S. R., Normal Electrocardiogram

Case 4: S. R., Coronary artery disease, Lt. Dominant artery

Fig. 30 Case 4: S. R., Coronary artery disease, Lt. Dominant artery, left main narrowing Case 4: S. R., Analysis result of normal ECG and diseased coronary artery group (lead 2)

Fig. 32 Case 5: L. Z., Normal Electrocardiogram

Fig. 33 Case 5: L. Z., Coronary artery disease, Lt. artery

Fig. 34  Case 5: L. Z., Coronary artery disease, Rt. artery

Case 6: F. M., Normal Electrocardiogram

Fig. 37 Case 6: F. M., Coronary artery disease, Lt. Artery with LM ostial stenosis Case 6: F. M., Coronary artery disease, Rt. Artery Case 6: F. M., Analysis result of normal ECG and diseased coronary artery group (lead 2)

ANALYSIS OF ELECTROCARDIOGRAM SIGNALS

RELATED APPLICATIONS

This application is a division of U.S. patent application Ser. No. 11/920,577 filed on Nov. 16, 2007, which is a National Phase of PCT Patent Application No. PCT/IL2006/000576 having International Filing Date of May 16, 2006, which claims the benefit of priority of U.S. Provisional Patent Application No. 60/681,431 filed on May 17, 2005. The contents of the above Applications are all incorporated herein by reference.

FIELD AND BACKGROUND OF THE INVENTION

The present invention relates to analysis of electrocardiogram signals and, more particularly, but not exclusively to a method and apparatus for enhancement of electrocardiogram signals, with clinical applications.

According to the world health organization (WHO) the leading cause of mortality and morbidity worldwide is heart disease. This fatal disease is a big challenge to the health system and the main goal is the detection of the disease at a young age (at the $4^{th}$-$5^{th}$ decades) when the mortality rate is higher. At the other end an early detection and diagnosis of the disease can lead to an effective treatment, which may lead to reduction in both mortality and morbidity for many people worldwide.

The Electrocardiogram as a Heart Diagnosis Tool

As the heart undergoes depolarization and repolarization, the electrical currents that are generated spread not only within the heart, but also throughout the body. This electrical activity generated by the heart can be measured by an array of electrodes placed on the body surface. The recorded tracing is called an electrocardiogram (ECG, or EKG). A typical ECG tracing for a single heartbeat is illustrated in FIG. 1. A waveform envelope 10 having several different components represents the heartbeat. The different components or waves that comprise the ECG represent the sequence of depolarization and repolarization of the atria and ventricles.

The P wave 12 represents the wave of depolarization that spreads from the SA node throughout the atria, and is usually 0.08 to 0.1 seconds (80-100 ms) in duration. The brief isoelectric (zero voltage) period 14 after the P wave represents the time in which the impulse is traveling within the AV node where the conduction velocity is greatly retarded.

The period of time 16 from the onset of the P wave to the beginning of the QRS complex is termed the P-R interval, which normally ranges from 0.12 to 0.20 seconds in duration. This interval represents the time between the onset of atrial depolarization and the onset of ventricular depolarization. If the P-R interval is >0.2 sec, a conduction defect (usually within the AV node) is present, a condition known as first-degree heart block.

The QRS complex 18 represents ventricular depolarization. The duration of the QRS complex is normally 0.06 to 0.1 seconds. This relatively short duration indicates that ventricular depolarization normally occurs very rapidly. If the QRS complex is prolonged (>0.1 sec), conduction is impaired within the ventricles. This can occur with bundle branch blocks or whenever a ventricular foci (abnormal pacemaker site) becomes the pacemaker driving the ventricle. Such an ectopic foci nearly always results in impulses being conducted over slower pathways within the heart, thereby increasing the time for depolarization and the duration of the QRS complex. The QRS complex comprises a short negative Q wave 18.1, a large positive R wave 18.2 and a short negative S wave 18.3.

The isoelectric period (ST segment) 20 following the QRS is the time at which the entire ventricle is depolarized and roughly corresponds to the plateau phase of the ventricular action potential. The ST segment is important in the diagnosis of ventricular ischemia or hypoxia because under those conditions, the ST segment can become either depressed or elevated.

The T wave 22 represents ventricular repolarization and is longer in duration than depolarization, meaning that conduction of the repolarization wave is slower than the wave of depolarization.

The Q-T interval 24 represents the time for both ventricular depolarization and repolarization to occur, and therefore roughly estimates the duration of an average ventricular action potential. This interval can range from 0.2 to 0.4 seconds depending upon heart rate. At high heart rates, ventricular action potentials shorten in duration, which decreases the Q-T interval. Because prolonged Q-T intervals can be diagnostic for susceptibility to certain types of tachyarrhythmia, it is important to determine if a given Q-T interval is excessively long. In practice, the Q-T interval is expressed as a "corrected Q-T (Q-Tc)" by taking the Q-T interval and dividing it by the square root of the R-R interval (interval between ventricular depolarizations). This allows an assessment of the Q-T interval that is independent of heart rate. Normal corrected Q-Tc intervals are less than 0.44 seconds.

There is no distinctly visible wave representing atrial repolarization in the ECG because it occurs during ventricular depolarization. Because the wave of atrial repolarization is relatively small in amplitude (i.e., has low voltage), it is masked by the much larger ventricular-generated QRS complex.

ECG tracings recorded simultaneous from different electrodes placed on the body produce different characteristic waveforms. The routine twelve leads electrocardiogram is an old and well-established technique and is very useful in every-day clinical activity. This method can show an active event like myocardial infarction ("heart attack") at its very acute stage or other cardiac ischemic events at time of occurrence (like in the so called "unstable coronary syndrome"). Routine ECG can also show that the heart underwent infarction in the past. This method cannot detect the existence of narrowing of the coronary arteries ("coronary disease") in a quiescence situation and can appear totally normal even though there is a sever underling disease. To detect the coronary disease prior to damage to the heart there are several provocative tests that bring the heart to a maximal workload while testing its response to the stress.

There are several routine "non-invasive" methods to detect and diagnose heart disease based on provocative tests. One method is electrocardiogram monitoring during programmed exercise aimed to achieve target high heart rate. Several electrocardiogram changes at the peak heart rate ("ST segment deviation") may indicate heart ischemia usually caused by narrowing of the coronary arteries supplying blood to the heart muscle. This method is not highly sensitive and it can detect the coronary disease in only 50-60%.

Another technique couples the programmed ECG monitored exercise with the injection of radio-nuclear compound (usually Thallium 207) at the time of peak heart rate. Reduction in blood supply to a certain heart segment diminishes the Thallium concentration in this segment. The radioactivity from the heart is detected by Gamma camera and a cold spot represent a segment with reduced perfusion due to narrowing in the coronary artery supplying this segment. The sensitivity of this method to detect coronary disease is 80-90% but it is an expensive method requiring high-price equipment that demands special training and a prolonged learning curve and is complicated by the need to use and handle radioactive compounds.

Another diagnostic method is the stress echocardiogram. This technique utilizes echocardiogram imaging of the heart during peak heart contraction achieved by either exercise or infusion of the drug dobutamine. Under this peak heart workload a reduction in contractility of a particular segment is an indication of reduction in blood supply to this segment due to coronary artery narrowing. This method has a sensitivity of 70-80%. Still the data acquisition requires expensive equipment, cumbersome detection and reading of the heart contraction and is associated with prolonged training and learning curve.

Recently there have been preliminary reports of the use of non-invasive multi-slice computerized tomography (CT) angiograms using X rays to detect coronary disease. This method can show the absence of coronary disease but the method has a low predictive value in detecting the disease and its severity. This is an expensive device and the patient is exposed to high amounts of contrast media and X ray radiation.

In the routine regular rest ECG in use the doctor is shown a series of ECG signals showing numerous heartbeats in succession obtained from 12 leads. Each lead records the heart activity from a different angle and shows 3 to 7 heartbeats in succession. The rest ECG using few heartbeats in each lead has limited diagnostic power. It can show damage to the heart in the past or the occurrence of an acute event such as evolving myocardial infarction ("heart attack") or rhythm disturbances. Rest ECG can be diagnosed as normal but the patient may have a severe coronary disease underlying. Thus the rest ECG has no prognostic power and it cannot detect coronary disease as long as the heart itself is not damaged. However by obtaining many heartbeats at each lead using this embodiment the ECG is enhanced and several new features emerge with better diagnostic and prognostic power.

There is thus a widely recognized need for, and it would be highly advantageous to have, an electrocardiogram monitoring and analysis system devoid of the above limitations.

SUMMARY OF THE INVENTION

According to one aspect of the present invention there is provided a method for graphical representation of a train of ECG complexes, the ECG complexes comprising an R wave and a T-P interval and having variable isoelectric baselines, the method comprising:

aligning the complexes in terms of signal amplitude by obtaining a baseline, thereby to provide a graphical representation of the train of ECG complexes; and aligning the complexes temporally using respective predetermined points.

Preferably, obtaining a baseline comprises aligning respective T-P intervals, and involves non-uniform sampling of the complexes. Such non-uniform sampling may for example take the form of statistically heavy sampling of the T-P part with statistically light sampling of the P-T part.

In an embodiment, the respective predetermined points are R waves.

The method may comprise obtaining the train from each one of a plurality of leads at different locations on a subject.

The method may comprise selecting between the alignments.

The method may comprise obtaining the train of ECG complexes using a sampling rate in excess of 1 KHz.

The method may comprise obtaining the train of ECG complexes as at least a sixteen bit signal.

The method may comprise carrying out the aligning of respective T-P intervals by use of polynomial cubic hermite splines.

The method may comprise associating the polynomial cubic hermite splines with knot points generated from linear regression of respective t-p intervals.

According to a second aspect of the present invention there is provided a method of displaying ECG representations of respective heartbeats of a patient comprising:

obtaining ECG signals of succeeding heartbeats from a patient, aligning the ECG signals, superimposing the signals, and displaying the superimposed signals, thereby to provide a representation of variations in an ECG signal over time.

Preferably, the superimposing comprises retaining shape information of the ECG representations such that the displaying the superimposed signals comprises displaying shape variation of the ECG signals.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The patent or application file contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a simplified diagram showing a single heartbeat using an ECG.

FIG. 2 is a simplified diagram illustrating an alignment unit according to a first preferred embodiment of the present invention;

FIG. 3 is a pulse histogram illustrating superposition of a sequence of ECG heartbeats from a single lead using the alignment unit of FIG. 2;

FIG. 4 is a simplified flow chart illustrating a process of obtaining an ECG visualization according to a preferred embodiment of the present invention;

FIG. 5 is a simplified diagram showing vectors of the heart sequence that can be obtained from different lead locations;

FIG. 6 is a flow chart showing the process of FIG. 4 in greater detail;

FIG. 7 is a simplified diagram showing the isoelectric level alignment unit of FIG. 2 in greater detail;

FIG. 8 is a simplified diagram showing the process of superposition according to a preferred embodiment of the present invention;

FIG. 9 is a simplified diagram showing directional vectors through a schematic heart;

FIG. 10 is a schematic representation illustrating a configuration for producing a vector plot according to a preferred embodiment of the present invention;

FIG. 11 is a simplified block diagram illustrating an ECG scanning and representation device according to a preferred embodiment of the present invention;

Figure 12:
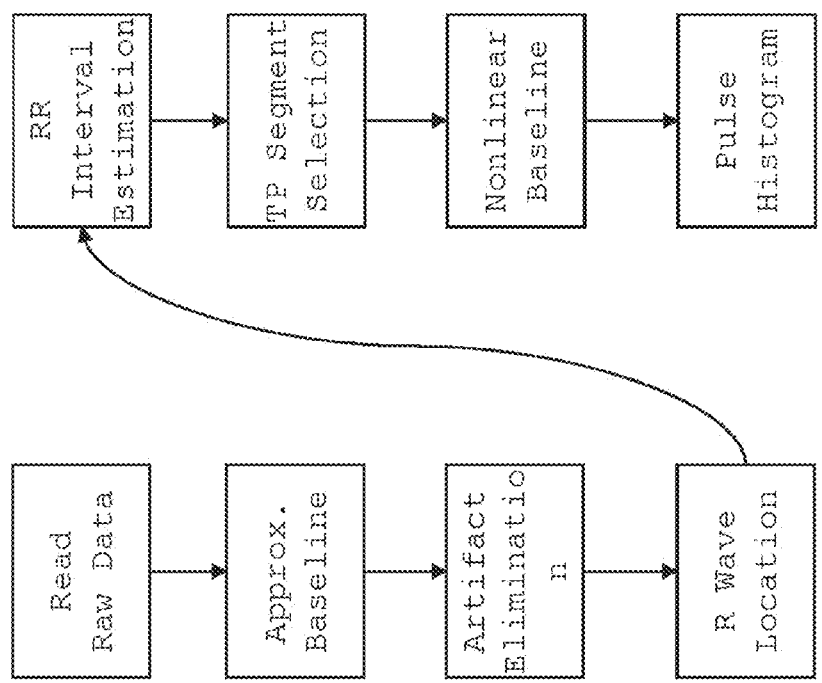
Figure 13:
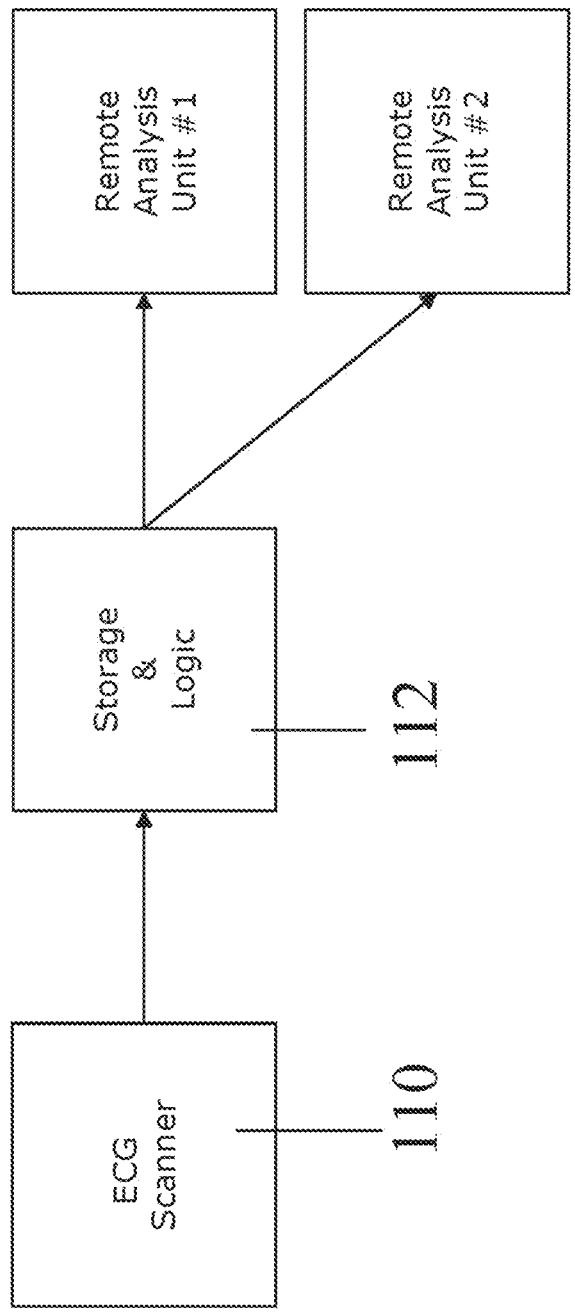
Figure 40:
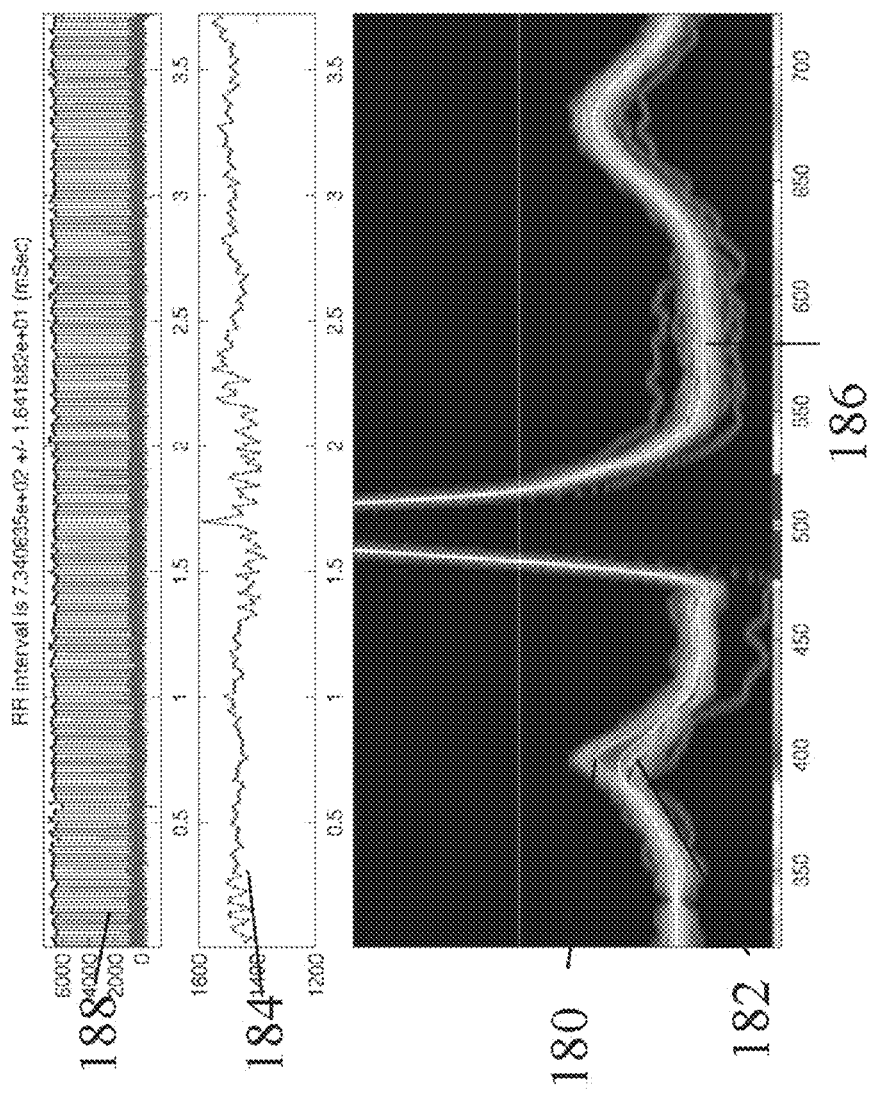
Figure 41:
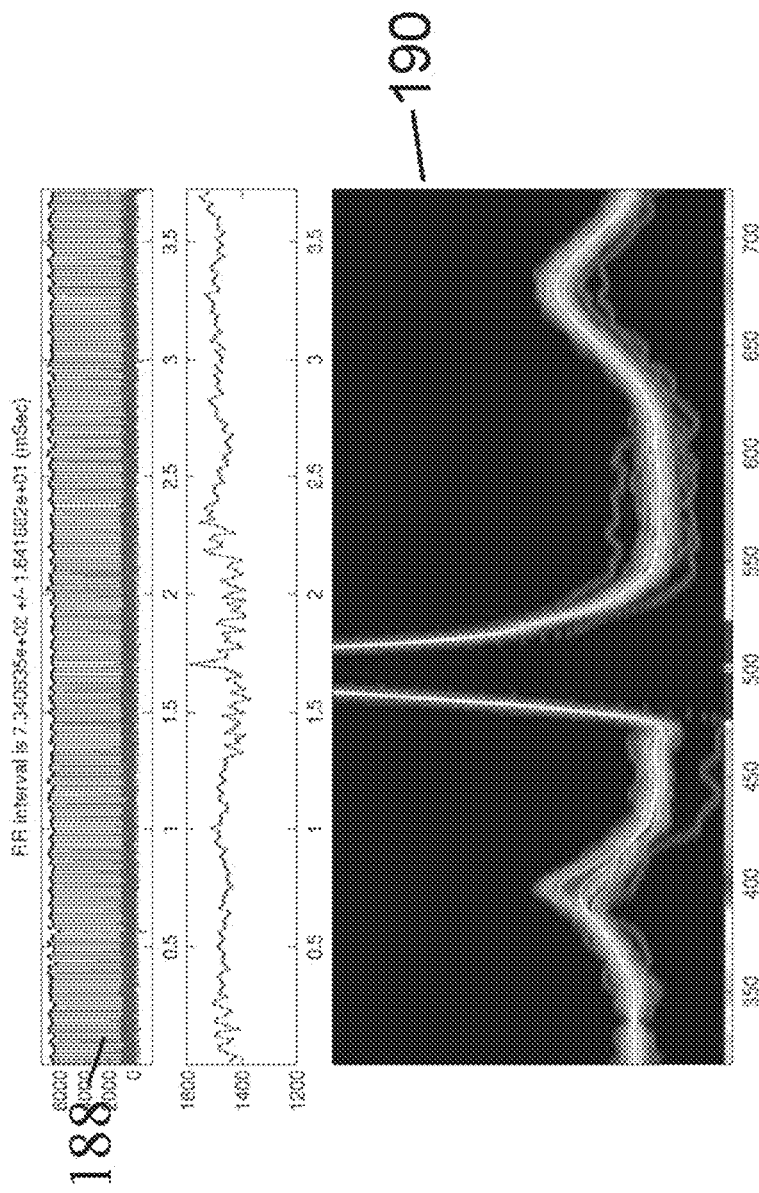
Figure 42:
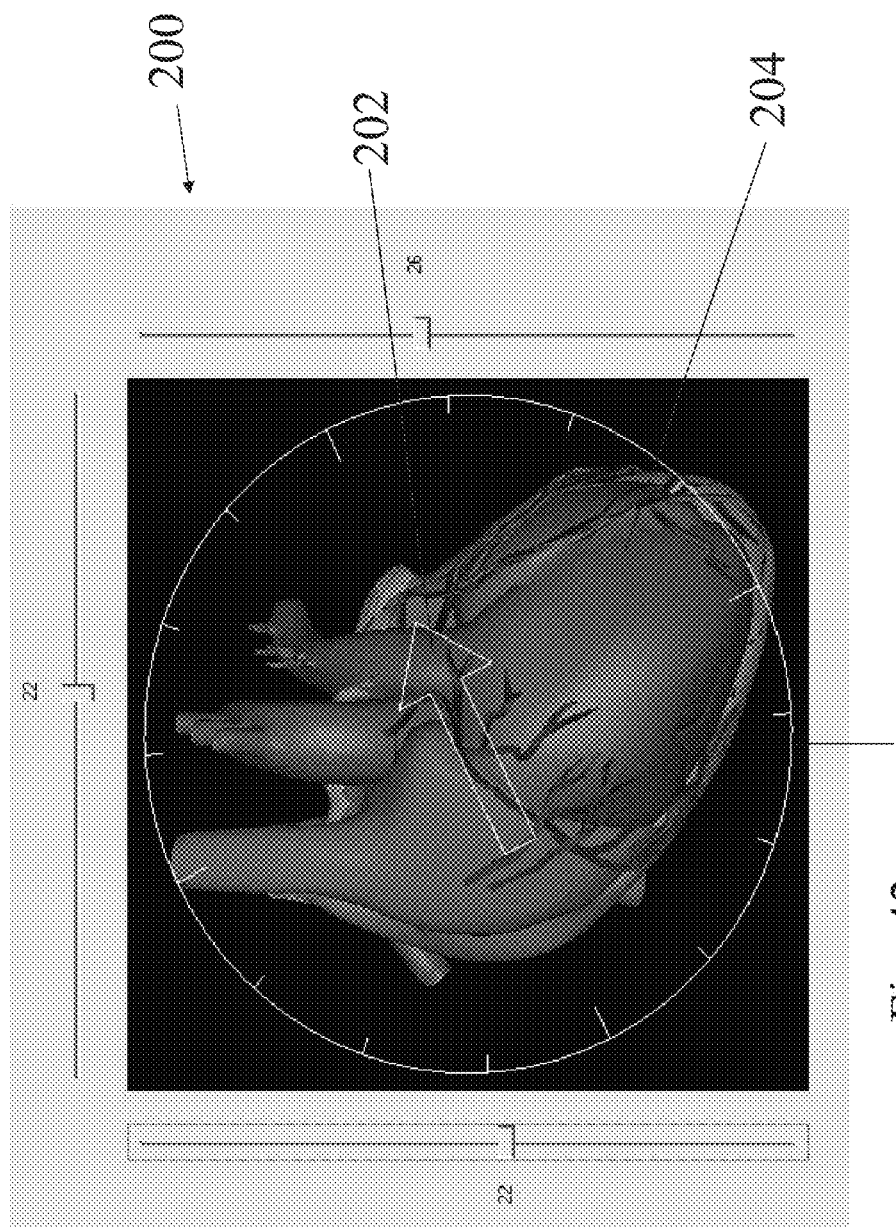

FIG. 12 is a flow chart showing a more detailed process for obtaining an ECG representation according to a preferred embodiment of the present invention;

FIG. 13 is a simplified diagram illustrating a configuration of the preferred embodiments suitable for remote monitoring;

FIGS. 14 to 39 illustrate six case studies of patients using the present embodiments;

FIG. 40 illustrates a plot according to a preferred embodiment of the present invention in which color separation is used to distinguish between short beats (short R_R) and long beats;

FIG. 41 illustrates a further plot according to a preferred embodiment of the present invention in which the value of including the R-R time plot is illustrated;

FIG. 42 illustrates a user interface screen according to a preferred embodiment of the present invention allowing the user to select a direction over the heart for a plot based on multiple leads.

Figure 43:
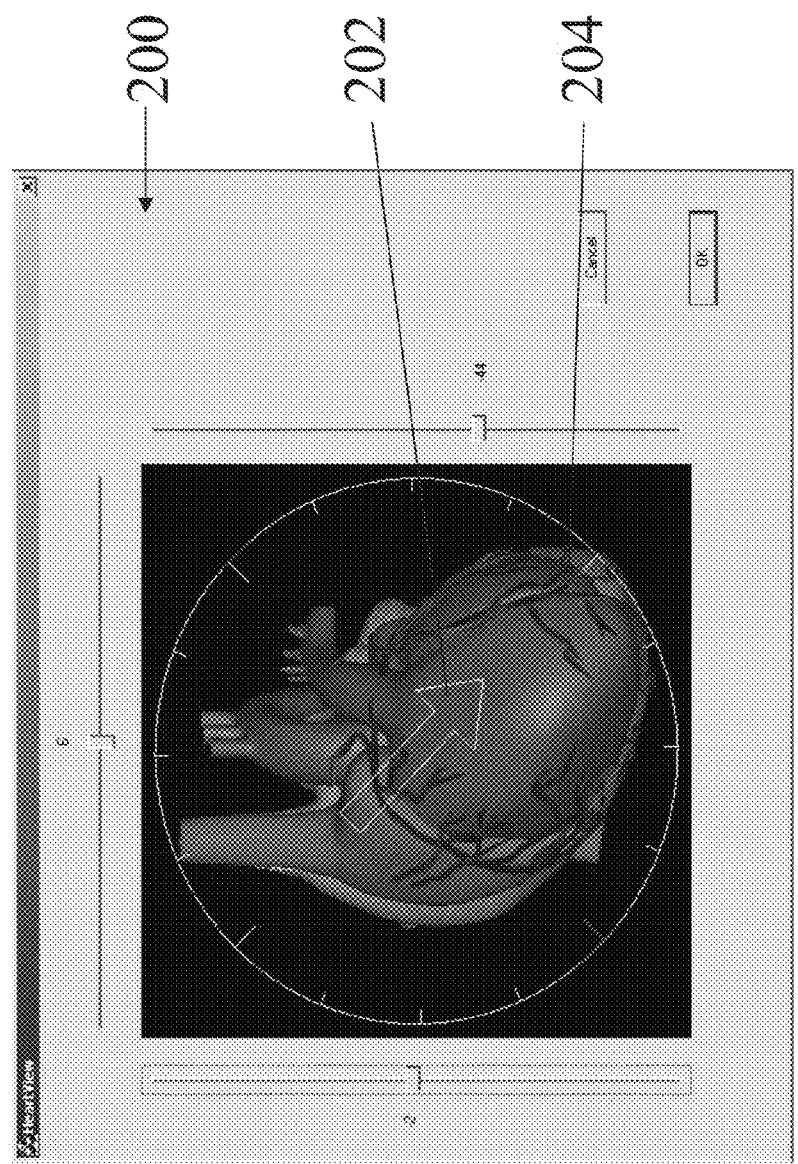
Figure 44:
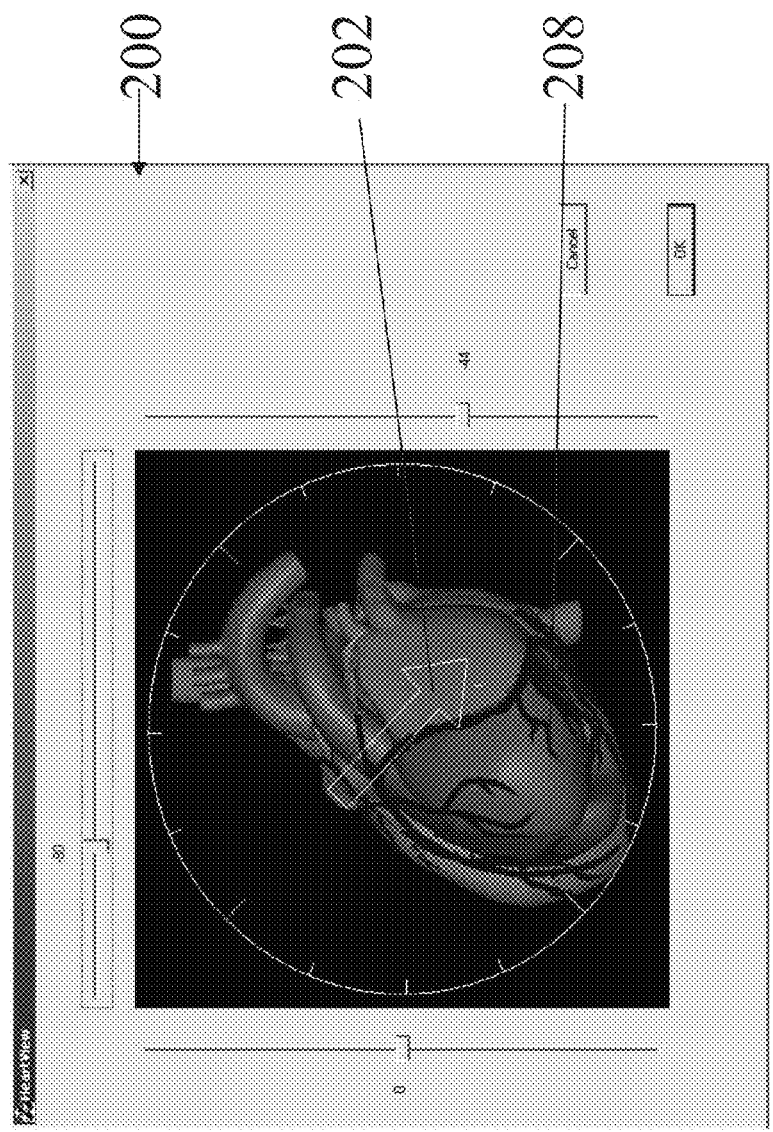
Figure 45:
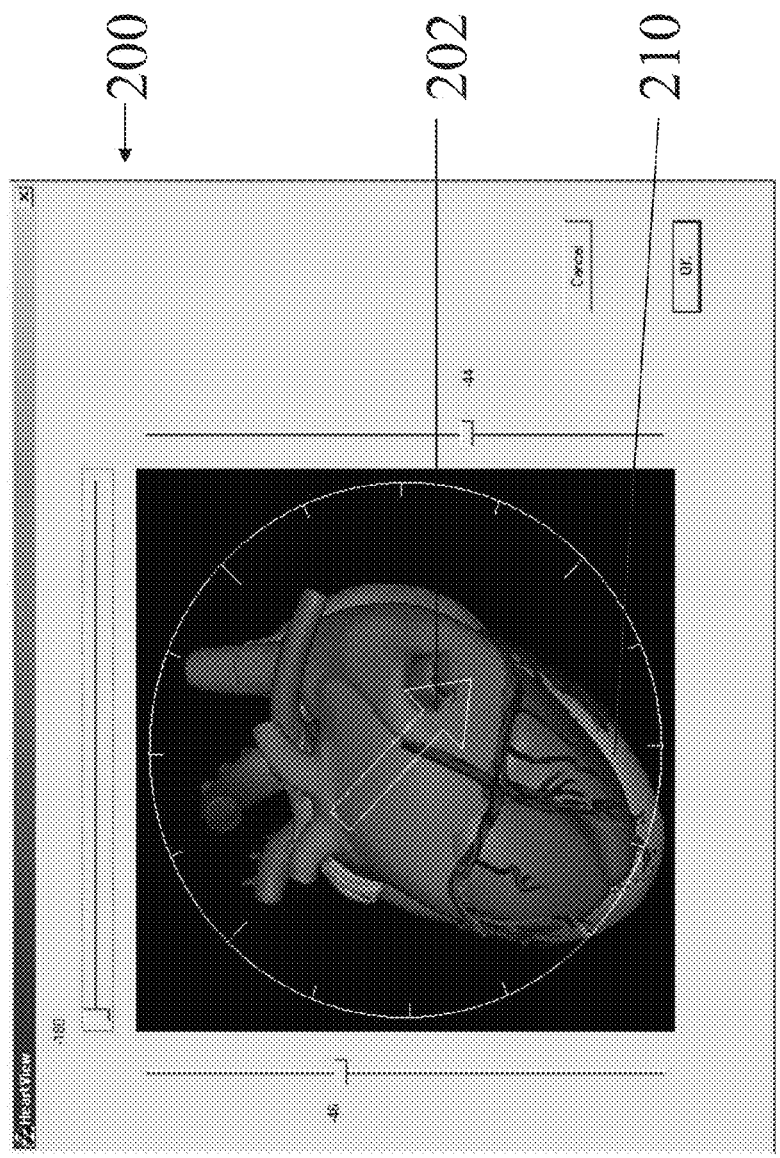

FIG. 43 illustrates the user interface of screen 42 in which the user has selected a different direction from that shown in FIG. 42;

FIG. 44 illustrates the user interface of FIG. 42 showing the heart from a different orientation; and FIG. 45 illustrates the user interface of FIG. 42 showing the heart from yet another orientation.

DESCRIPTION OF THE PREFERRED EMBODIMENTS

The present embodiments comprise a representation of the ECG signal in which the R wave on the time axis and the T-P interval on the amplitude axis are used to project a plurality of ECG complexes into a single complex.

The projection involves baseline generation, and it is noted that LTI (linear time invariant) methods cannot be used. LTI methods treat the entire ECG signal the same way. The present inventors realized that when obtaining a baseline, the P-T portion of the complex is preferably ignored. The alignment allows a visualization of the ECG which is based on the superposition of these aligned complexes in a way that makes variation between complexes easy to see.

The principles and operation of an ECG representation system according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1:
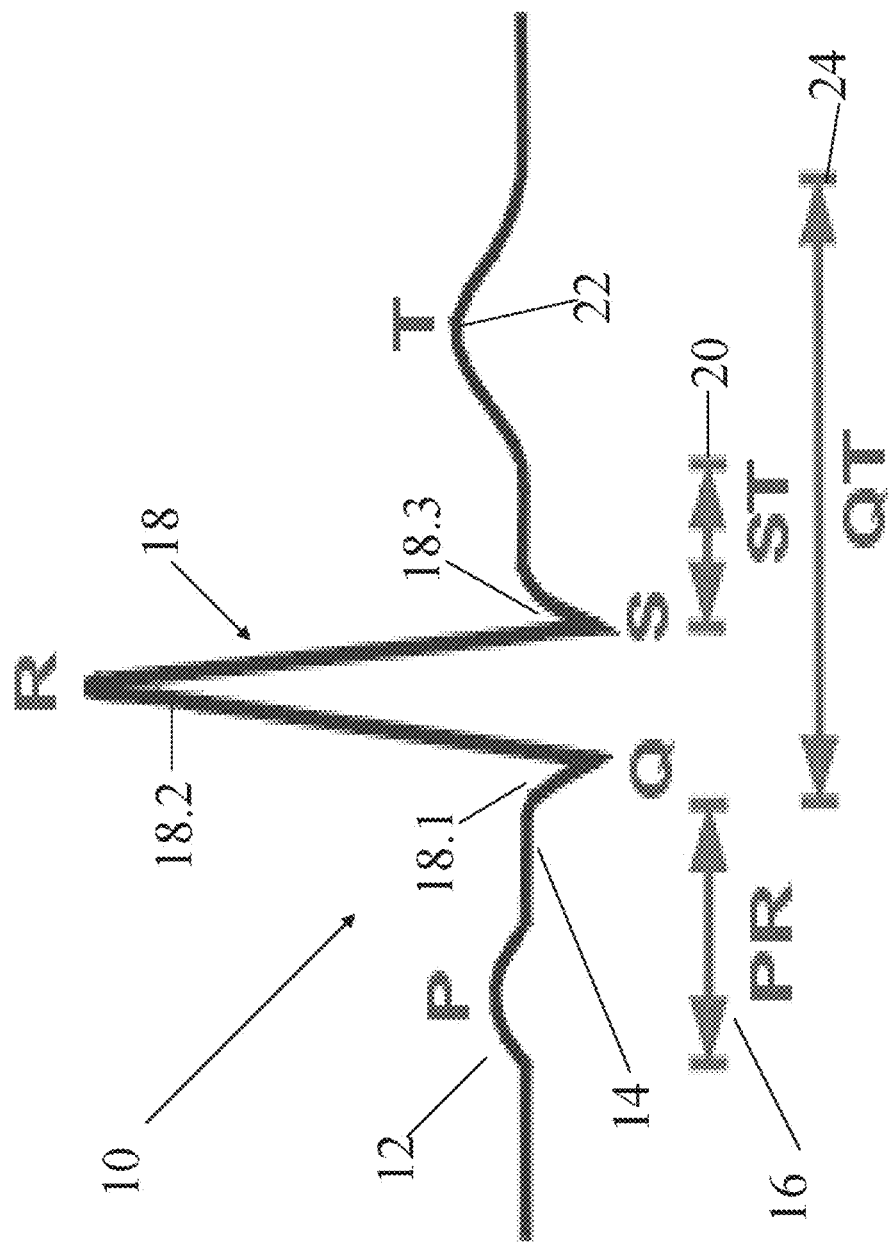
Figure 2:
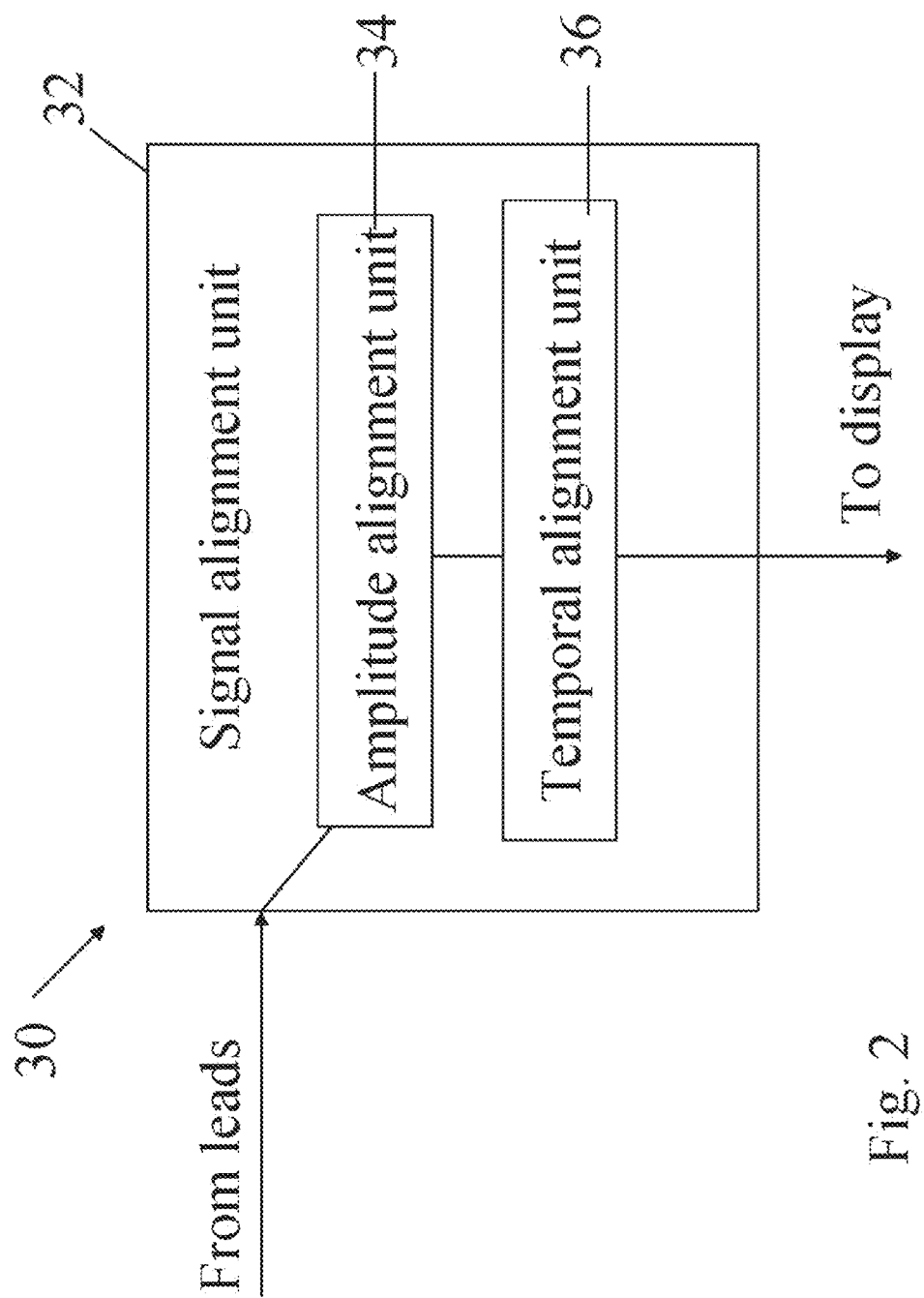

FIG. 1, which illustrates a standard ECG signal, has been referred to above. Reference is now made to FIG. 2, which is a simplified diagram illustrating apparatus according to a first preferred embodiment of the present invention which takes ECG signals as an input, carries out signal processing as will be described hereinbelow, and provides a graphical representation of a train of ECG complexes. The ECG complexes comprise all of the features of a typical ECG complex, in particular an R wave and a T-P interval, and it is added that the different complexes have variable baselines, that is have different isoelectric levels, generally making simple superposition of the signals meaningless. The apparatus aligns the different complexes so as to superimpose one over the other so that a single construct illustrates the entire train of heartbeats. The apparatus 30 which achieves the superpositioning of the ECG complexes comprises a signal alignment unit 32. The signal alignment unit 32 has, at least from the functional point of view, two components, an isoelectric level alignment unit 34 which aligns the complexes in terms of isoelectric level, and a temporal alignment unit 36 which aligns complexes temporally using a preselected point on the R wave as an alignment reference. Essentially the R wave is used for alignment along the X axis. The isoelectric level alignment, or alignment in the Y axis, is achieved by aligning T-P intervals between succeeding complexes. By the term "succeeding" is intended those complexes which follow on in a series, irrespective of whether they are actually adjacent in the series, or whether there are intervening complexes that are for example not processed. The two alignment units work together to provide superposition of the succession of ECG complexes, and the superposition represents the course of the heartbeat over a period of time.

Figure 3:
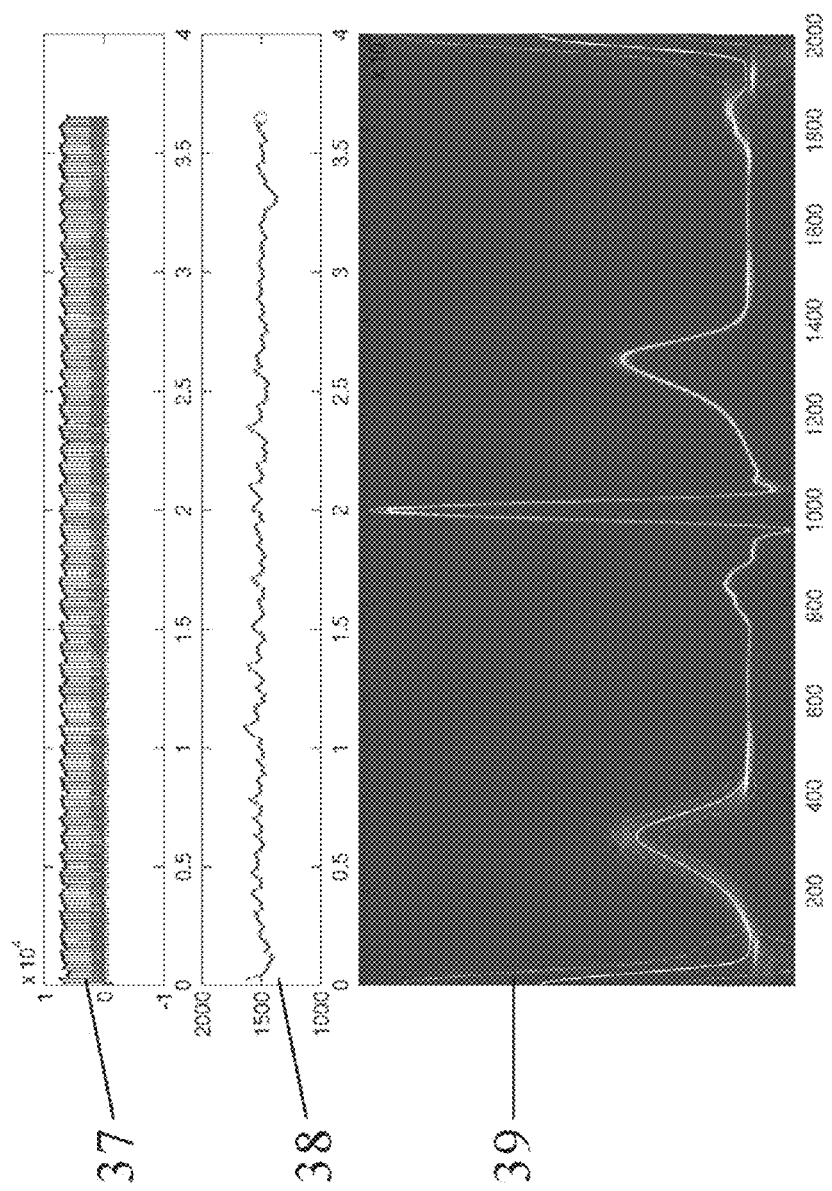

The individual heartbeats or ECG complexes vary both in terms of timing and in terms of isoelectric levels and therefore cannot be aligned in any obvious way. However, if aligned separately in both the X and Y axes using alignment unit 32, as set out above, then a meaningful superposition is produced. An example of the resulting superposition of multiple ECG complexes is shown in FIG. 3. The superposition shows all of the features of FIG. 1 in a single plot.

In more detail, FIG. 3 is a screen showing three plots numbered respectively upper plot 37, middle plot 38 and lower plot 39. The upper plot is a compressed version of the full ECG scan as for example shown below in FIG. 14 and is retained in order that the raw ECG information can be referred to as necessary. Middle plot 38 is an R-R time plot which plots the R-R interval against time and thus gives immediate indication of heartbeat timing irregularities. That is to say the R-R time plot should be smooth in a healthy individual, merely curving up or down in the event of increase or decrease of stress.

In the lower plot 39, the full succession of heartbeats is represented by a single graphical representation produced by overlaying aligned QRS complexes. The representation saves the doctor from having to look at a train of beats to see changes. In general, if the superposition is sharp, the beats are similar, but if the superposition is fuzzy, then the heartbeats are not faithful copies of one another and further investigation is required. The information about what is wrong is present in the superposition in a form that will be apparent to a doctor trained to deal with conventional ECG readouts since the form of the readout is preserved. The plot shows an average of the ECG signal as a white central line in the plot. A surrounding area of gray (when shown in black and white) or red (when shown in color) gives one standard deviation, and a dotted line around the plot indicates the extent of the second standard deviation.

The plot thus indicates the stability of the heartbeat signal over time. In the absence of stability the plot readily indicates the variation. As well as the indication of variation inherent in the plot, it is additionally possible to embed markers emphasizing the variation into the display of the plot, as will be explained in greater detail below.

In an embodiment, the train of ECG complexes is obtained separately from each one of several leads at different locations on a subject. The electrical changes induced by heart activity are directional, and thus electrodes at different locations on the subject show the heartbeats from different perspectives. The graphical representation system can be used to provide separate alignments or superpositionings for each of the leads.

In the device output, a selector, which may be software or hardware, may allow a user to select between the different alignments.

The pure ECG signals received at the electrodes are preferably obtained using an oversampling feature. The oversampling feature obtains the train of ECG complexes using a sampling rate in excess of 1 KHz. As a result it picks out features of the ECG that conventional sampling often misses, and the superposition is able to show trends in that feature.

The actual signals as picked up by the leads are of course analog waveforms but in a preferred embodiment they are digitized prior to processing by the alignment unit. Following digitizing, the oversampled train of ECG complexes may be digitized as a sixteen bit or higher precision signal at an appropriate sampling rate in order to retain the required information.

As will be explained in greater detail below, isoelectric alignment unit 34 is configured to carry out alignment of respective T-P intervals by use of polynomial cubic hermite splines. The polynomial cubic hermite splines are associated with knot points generated from linear regression of respective t-p intervals. This is in contrast to current devices which generate a baseline by spectral filtering of the ECG signal. Such filtering obscures many details that the presently preferred embodiments are able to supply.

In an embodiment, the analysis unit may be located remotely from a subject. It may thus connect to the subject via a communication link. The communication link may be a network able to link two or more subjects to a single measurement apparatus. That is to say, all that is required to occur at the subject is to obtain the ECG signals using leads. The processing stage may be carried out by an analysis unit located elsewhere in the hospital or even away from the hospital, say at a central computing location that provides services for multiple doctors and clinics. As the processing apparatus is the more expensive part of the system, the present embodiments allow a cost-effective way of providing ECG monitoring, in contrast to the current trend which is to provide integrated units which have to present with the subject.

Using such a remote system, the raw ECG data may be transmitted from a remote scanner, for example in the accident and emergency department or in a doctor's office, to a central processing facility, and provided for remote analysis by one or more cardiologists.

Remote monitoring units may likewise be remote stations of the central processing facility, or monitoring may be provided at the central processing facility. The central facility or the remote monitoring units as appropriate, run the visualization and analysis software of the present embodiments. In one preferred way of using the invention, the particular patient's data may initially be sent to two cardiologists, whose diagnoses are compared by the server's logic system. If the diagnoses do not agree, the system may automatically present the data to a third cardiologist and so on until agreement is reached.

The system design as described above has particular advantages over the current art, since the current art typically combines the analysis features with the data collection—making the data collection device unnecessarily costly, and requiring both the analysis unit and the medical specialist to be geographically close to the data collection device.

Figure 4:
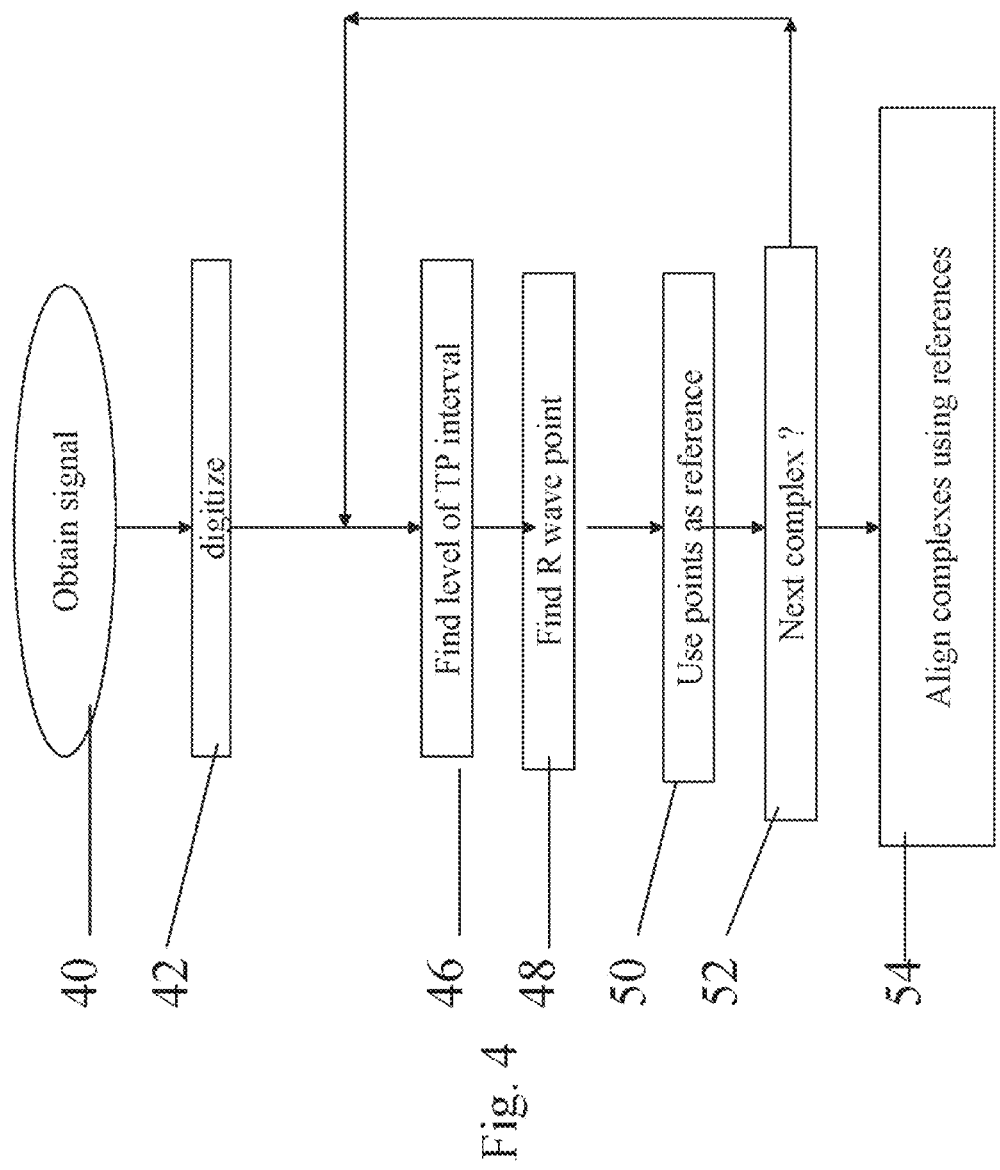

Reference is now made to FIG. 4, which is a simplified flow chart illustrating operation of the signal processing apparatus of FIG. 2 to carry out superposition of a series of ECG complexes from a subject. FIG. 4 shows a method for graphical representation of a train of ECG complexes. The method comprises obtaining the ECG signal from the lead, stage 40, and digitizing in stage 42. The stage is followed by an isoelectric alignment stage 46 which involves the TP interval and recognizing the isoelectric level at the TP interval to use as a baseline. For each of the complexes, a preselected point on the R wave is identified in stage 48 to use as a horizontal or temporal alignment point. The R wave point and the TP interval level are then marked as reference points in a stage 50 and the procedure is repeated for the following complexes in stage 52. Finally in stage 54 the different complexes are aligned.

Whilst FIG. 4 shows all of the complexes being aligned after all of the complexes have been referenced, it will be appreciated that as an alternative the complexes could be aligned one over the other as they are received, so that the development of trends is seen in real time.

Typically twelve leads are used, and each lead provides a slightly different perspective on the developing sequence of the heartbeat, as explained above.

The doctor is preferably enabled to select between the different alignment choices for different leads.

The overall system is now considered in greater detail.

ECG Basics

The electrocardiogram, as represented by FIG. 1, is a diagram representing the electrical activity of the heart, as measured from one or more leads attached to a patient's body. Leads are attached to the limbs and the chest.

The heart is a specialized muscle, and like all muscles its operation requires a flow of ions across cell membranes. Since ions are electrically charged, their accelerations generate a change in the surrounding electrical field. In heart muscles, the dominant electrical effect is caused by muscle depolarization—but repolarization is also significant.

Healthy heart activity causes depolarization and repolarization in a predictable pattern. As the interface between polarized and depolarized muscle moves across the heart, it induces a change in the electrical field in its direction of motion. The direction and magnitude ("vector") of the depolarization wave can be read from the ECG recordings.

Figure 5:
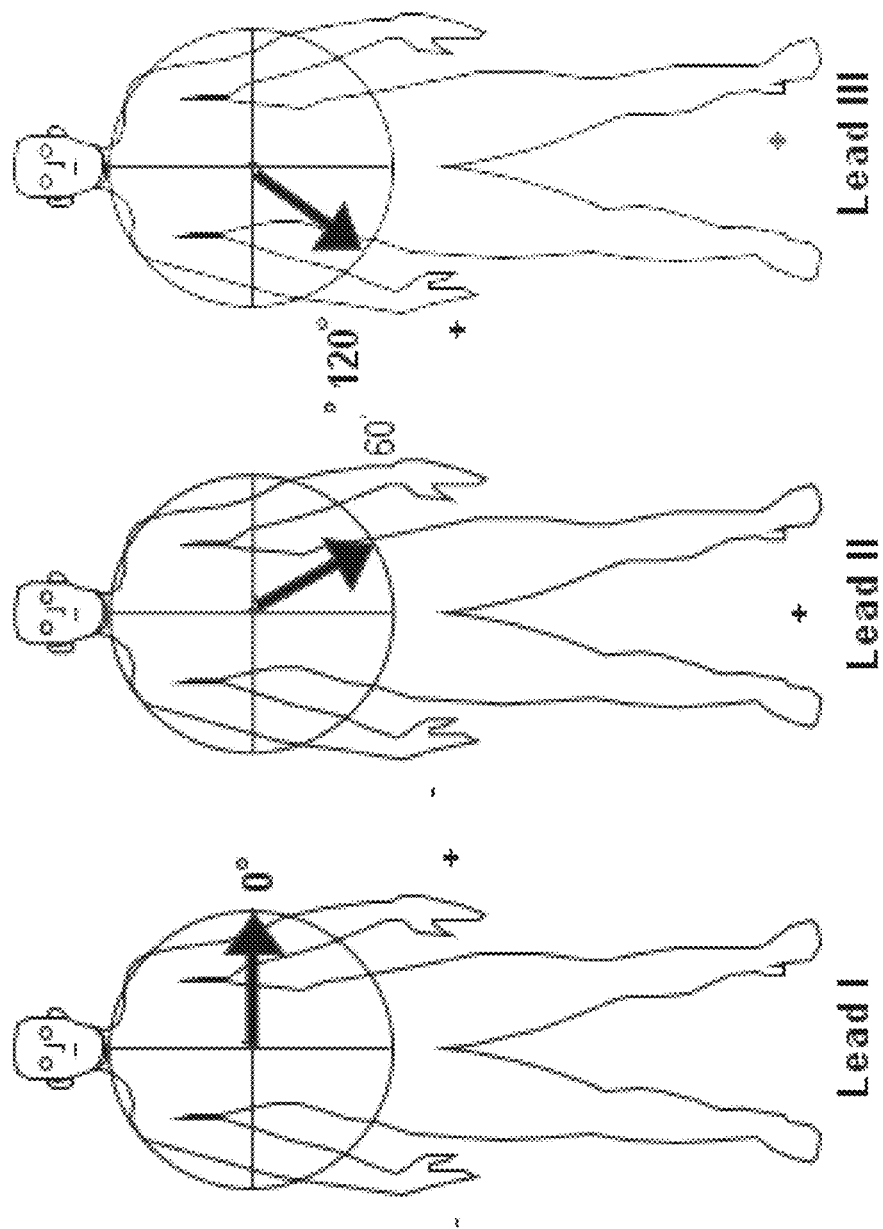

Reference is now made to FIG. 5, which shows a simplified case of three leads placed on a human body at different locations. The different leads detect electrical potential differences between different points on the skin, thereby obtaining projections of the heart's electrical activity in various directions. For example, lead I gives a horizontal projection of the electrical field.

Various changes in the ECG over a sequence of heartbeats, or absolute changes in the ECG for a given patient, are diagnostic for specific heart conditions. Using the conventional representations however, even the most skilled electrocardiologist may miss some signs of trouble, since some of the changes are fairly gradual, and certain key features do not always show up clearly on conventional displays. The ECG Visualization method of the present embodiments makes symptoms within the ECG more readily apparent, and thus enables doctors to analyze ECG-s faster and with fewer errors.

Structure of ECG Signals

All ECG signals are differential—they express changes in the electrical field rather than its absolute value. In order to interpret a raw ECG recording, it must first be normalized relative to an isoelectric baseline which represents the electric field present without heart muscle activity.

Once normalized relative to the isoelectric baseline, a healthy ECG shows its characteristic structure as illustrated in FIG. 1, which consists of a complex of five or six "waves" for each heartbeat. Each "wave" represents a characteristic portion of the ECG waveform.

The waves are denoted by letters of the alphabet, as taken in chronological order within a heartbeat. The first wave is denoted by the letter 'p', and subsequent waves are denoted by the subsequent letters of the alphabet. In cases where the relative sizes of the waves are important, capital letters are used to denote higher amplitudes.

The highest frequency component of a beat is usually the "qrs complex" of the beat. Often this complex also has the highest amplitude, with R waves showing the most significant deviation from the isoelectric. R wave peaks are used in the present embodiments as the nominal times for heartbeats because these features make them the easiest to locate, and the "R-R Interval" is used as the standard measure of beat to beat time interval (reciprocal of the heart rate).

Some Practical Aspects of ECG Measurement

ECG activity is of the order of single micro-volts (when measured externally). Thus high amplification is required in order to resolve any features of the signal. High amplification gain also entails high levels of noise, and the combination of high amplification and the moving baseline of the ECG signal also raises issues of input saturation.

Sources of noise in ECG signals include:
Natural variability in body conductivity, caused by body fat and other physiological factors.
Patient movement.
Ambient electrical fields, most importantly the 50 or 60 Hz signal induced by AC power lines.
Measurement noise inherent in the measurement instrument.

Traditional signal processing techniques, such as analog and digital filters, do not perform very well on ECG signals. Such filters are designed to be linear, and thus they operate independently on the various frequency components of the ECG signal. However the ECG signal has a broad spectrum—containing significant energy in frequencies as high as 200 Hz and as low as 0.25 Hz. Much of the noise (e.g. AC induction noise at ambient frequency) shares the same spectrum, making it difficult to use a linear filter without degrading the ECG signal itself.

ECG Visualization Process

Figure 6:
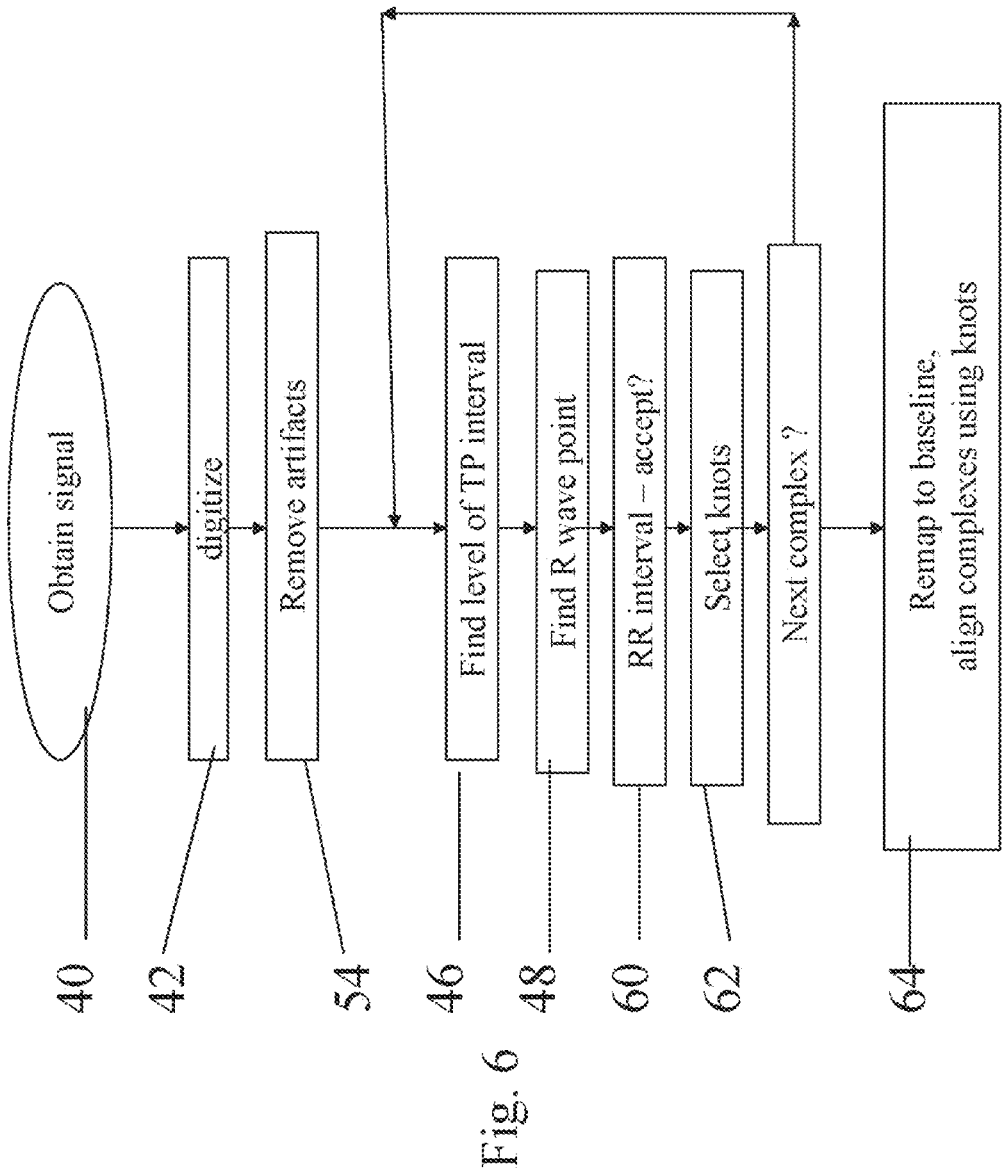

ECG recordings are visualized by the visualization software (VSW) according to the above described embodiments using the process of FIG. 6, which is a modification of the process of FIG. 4. Parts that are the same as in FIG. 4 are given the same reference numerals and are not referred to again except as necessary for understanding the present embodiment.

(1) The analysis system reads the raw ECG samples from the recording instrument in stage 40. This step includes digitization, which may occur on either side of the connection.
(2) The operator preferably removes any extreme artifacts from the recording in stage 54.
(3) An approximate isoelectric baseline is obtained based on the TP interval using a digital filter in stage 48.
(4) The starts of individual beats are detected by locating a predetermined point on the R wave in stage 46.
(5) In stage 60 the analysis unit computes the R-R interval—the interval between two beats—and uses it to decide which beats are good and which may corrupted too badly to use for further analysis.
(6) The operator selects knot points in stage 62 to use for baseline computations. These are points that are on the isoelectric baseline according to the operator's interpretation of a portion of the ECG signal.
(7) The ECG beats are remapped in stage 64 to the new baseline, superimposed and shown in pulse histogram form.
(8) The analysis unit provides various analysis aids to the operator, including the ability to zoom in on portions of the ECG signal, and to measure diagnostic parameters.
(9) The analysis unit provides the ability to display different groups of beats in different colors (e.g. red and blue) providing a contrast enhancing pulse histogram allowing the doctor to see differences between the two groups. Preferably this ability is used to compare between beats that follow a short R-R interval and beats that follow a long R-R interval, thereby allowing the doctor to see how the heart response changes in response to stress.

Reading ECG Samples

ECG samples are provided by the data processing centre in binary format. Packages of ECG data are sent over a network. If required the data may be signed and encrypted. The data is preferably sent to a specific cardiologist's monitoring unit and identified only by an occurrence identifier. Security features preferably ensure that unencrypted medical data is only available on the cardiologist's workstation and in the centre's databases.

The data format is preferably a "flat file" consisting of a fixed header and a series of 16 bit unsigned integers in little-endian format.

Approximate Baseline Acquisition

Figure 7:
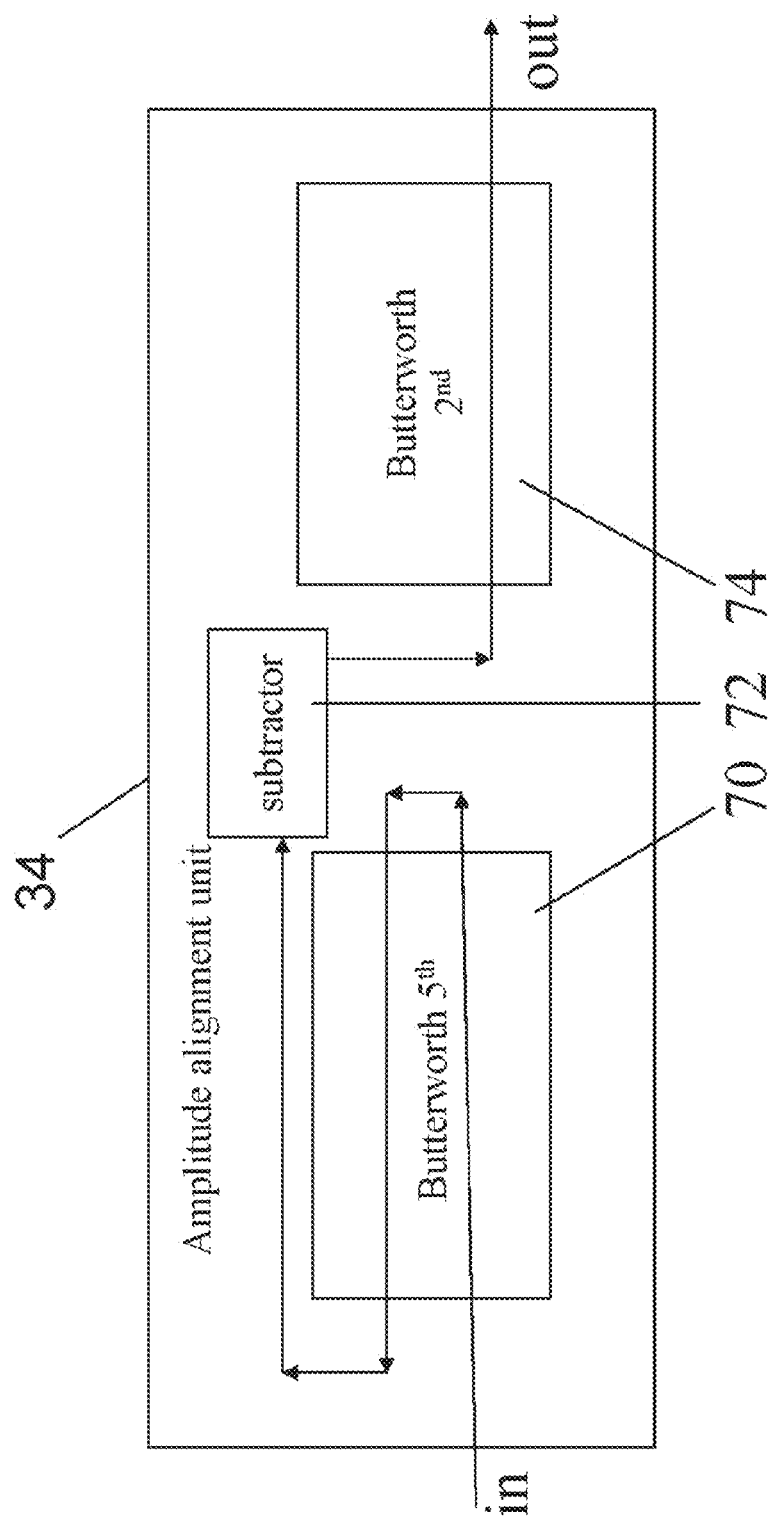

Reference is now made to FIG. 7, which illustrates a preferred construction of the isoelectric alignment unit 34. A fifth order Butterworth filter 70 is connected in series with a subtractor 72 and a second order Butterworth filter 74. In use, an initial baseline estimate is preferably created using the $5^{th}$ order Butterworth low-pass filter at $2 \times 10^{-3}$ cycles applied twice, once in temporal order and then in inverse temporal order to achieve zero phase shift. The initial baseline estimate is then subtracted using subtractor 72 from all samples to bring their isoelectric level close to 0. This filtered signal is further smoothed by mild $2^{nd}$ order Butterworth filter at 0.25 cycles, also applied once in temporal order and then in inverse temporal order to achieve zero phase shift.

The combination of these filters is equivalent to a bandpass filter with asymmetric rejection outside the passband. The outcome of the filtering process is referred to as the approximate signal hereinbelow.

Artifact Elimination

The system operator preferably selects portions of the approximate signal to be rejected from further analysis. Typically such rejected portions contain extreme transients cause by patient movements and other artifacts that would render whole portions of the ECG unusable. In a further preferred embodiment certain of these artifacts may be detected automatically.

R Wave Detector

In an embodiment, the operator may select to use either R waves or S waves for beat detection. For simplicity, the following describes the process for R waves only, however the skilled person will appreciate that the detection of S waves is identical, except for first reversing the sign of the signal.

R waves are detected by thresholding the approximate signal. The operator selects a threshold above which in his judgment the signal consists only of R "peaks". In certain cases, there may be R waves in which the R peak is small relative to p and t. In such a case an additional high-pass filter may be applied to emphasize the R waves. In a further preferred embodiment such a threshold may be determined automatically, using pattern recognition techniques. It is noted that there is an advantage to aligning the isoelectric levels prior to detecting the R waves.

The portions of the signal inside each R peak are detected using the threshold; the prior application of the mild lowpass filter to the approximate signal implies that the transition across the threshold is rarely noisy. The peak's sample index is taken to be the weighted average of the sample indices inside that peak, weighed by the difference between the sample and the threshold. Since the peaks are usually fairly close to a parabolic shape, the weighted average provides an unbiased estimate of the peak location.

The peak location is referred to as the beat time hereinbelow.

R-R Interval Detection

R-R intervals are computed by taking the median R-R interval between R waves in uninterrupted portions of the approximate signal. A median is used instead of a mean because of its superior rejection of outliers.

R-R intervals smaller than one half or larger than twice the median R-R are taken to be anomalies, and flagged as such to attract the operator's attention.

After completing the R-R interval detection, the analysis system achieves superposition by overlaying one R-R interval on each side of the beat time of every beat (or a large sampling of beats, if the signal is very long). This is the "overlay plot" of the approximate signal.

T-P Baseline Segment Selection

The operator may now use the overlay plot to indicate a segment of the signal that lies between the t (or u) of the previous beat and the p of the current beat. This segment is preferably wholly on the isoelectric baseline, in the operator's judgment.

The current implementation allows the operator to select two such segments—one before the beat and one after the beat. Obviously, the baseline after beat N is the baseline before beat N+1—which means that most of the time only the first segment is used. The second segment is used when the next beat would occur in a rejected region of the signal.

Because the baseline is electrically constant in the heart, the baseline segments between beats typically show only some low-frequency modulation (of the order of 1 Hz or less) and electrical noise. It contains none of the spectral complexities of the entire ECG signal. Thus it is well suited for further automated processing.

Nonlinear Baseline Estimation

Now that baseline time segments have been identified before and after each beat, these are used to obtain better baseline voltage estimates. First, the system computes a trend-line for each T-P baseline time segment by linear regression of the raw[1] ECG signal in that segment. It is noted that one should go back to the raw signal, because the spectral processing of the approximate signal corrupts the true baseline.

The trend-line is used to generate two knot points for a baseline spline. The knot points are taken to be points on the trend-line, 20% inside the baseline segment on each side. A cubic Hermite polynomial spline (a.k.a. PCHIP spline) is used to interpolate baseline values between the knot points. This spline is then used as the base-line for the final ECG visualization result.

The baseline is subtracted from the raw ECG signal, and the mild low-pass filter of FIG. 7 is applied to the result. The outcome of this computation is referred to hereinbelow as the calibrated ECG.

Theory Behind Baseline

The theoretical justification for using linear regression and polynomial interpolation instead of traditional signal processing tools is that the problem being solved is one in which we have highly non-uniform sampling of the system being measured. In baseline estimation we are looking for a good estimate of the voltage that would have been measured without any heart activity. We take the position that this voltage is measured at the full sampling rate in each baseline segment, and is not sampled at all within the heartbeat waveform itself. The most naïve model for interpolating such a smoothly varying baseline given segments of measurement, would be to use a polynomial patch between the measured segments—and in essence, this is what we do. This position is fundamentally different from baseline detection using analog filters, digital LTI (Linear Time Invariant) filters and digital adaptive filters that treat the ECG signal as essentially uniform.

Alternative embodiments of the baseline estimation method involve other methods suitable for non-uniform sampling, such as: approximation in shift invariant $L_p$ spaces, ARMA modeling, timing controlled adaptive filtering and Kalman filtering.

Pulse Histogram Generation

The calibrated ECG, exemplified by FIG. 3, is displayed using a pulse histogram visualization. The pulse histogram is generated using the process shown in FIG. 8 to which reference is now made. The outputs of the alignment procedure are obtained in stage 80. Then a histogram of the calibrated ECG values for the various offsets within one R-R interval from the beat time is generated in stage 82. The resulting matrix (taking each histogram as a column) is then convolved with a Gaussian blurring kernel in stage 84, and the logarithm of the result is obtained in stage 86 and used to assign pixel colors in stage 88, which is followed by display in stage 90.

The convolution is required for obtaining a good result, because of the following statistical reasons:
1. There is some inherent timing noise, i.e. error in locking on to the beat times.
2. There is some measurement error in the voltage 3. In places where the ECG signal changes, these two errors mix—timing errors can become voltage errors and visa versa.
4. The voltage at some fixed offset from the beat-time is assumed to obey some smooth distribution, of which the calibrated ECG values are only samples.

Generating Contrast Enhancing Pulse Histograms

Figure 8:
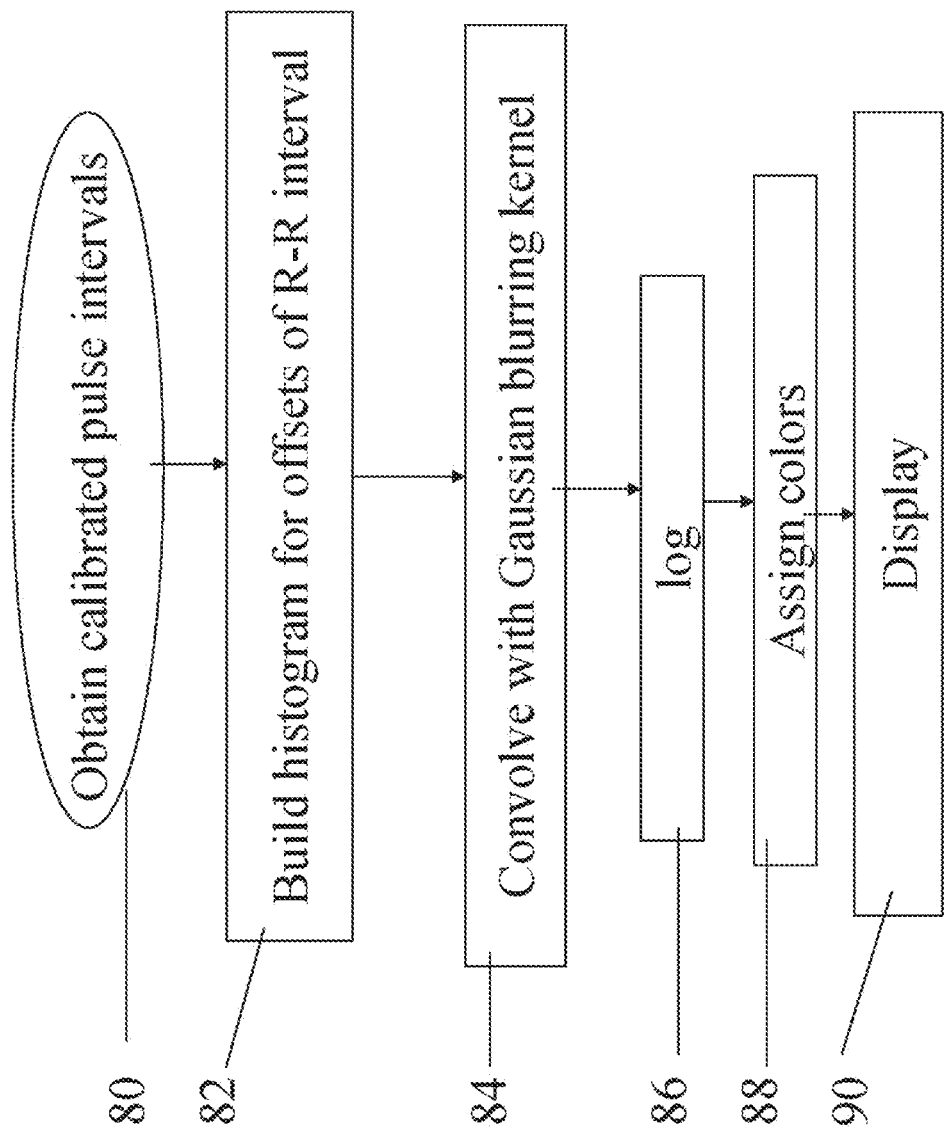

Contrast Enhancing Pulse Histograms are generated by performing the sequence described in FIG. 8 and above for each group separately up to stage 88 therein. At this time colors are assigned separately to different groups. In a preferred embodiment such colors are assigned in such a way that the overall luminance of a pixel reflects the sum of the log-probabilities obtained from all groups, so that the hue of the pixel indicates the extent to which the individual pixel is likelier to belong to one group more than the other. For example, with two groups colored red and blue: a bright blue pixel is common to most of the blue group but rare in the red group; a dark red pixel is found only in the red group, but is rare even there; a grey pixel is fairly common and found in both groups to an equal extent.

The following sections describe particularly preferred features of the present embodiments.

Oversampling

A preferred embodiment samples at 16 bits, 2 KHz or more for an extended duration (e.g. 3 minutes). This is much higher resolution in both time and voltage, and much longer duration than that used in most ECG examinations. This is referred to hereinabove as oversampling.

The oversampling is intrinsically connected with the display method since such an abundance of raw data would be difficult to interpret without the display features of the present embodiment, and this is believed to account for why prior art has apparently never made use of such oversampling.

Nonlinear Baseline

The standard or spectral approach for obtaining a baseline is equivalent to the first stage of baseline computation in the present embodiments. The embodiments however make use of the realization that spectral methods are insufficient for obtaining a high quality baseline, and go on to provide a better baseline in practice. The improvement in baseline quality enables the system to filter out baseline noise that would otherwise hide important diagnostic symptoms, as appears to happen in other ECG devices.

As explained above, the baseline computation of the present embodiments make use of Polynomial Cubic Hermite splines, that are associated with knot points generated from a linear regression of t-p interval between beats. The temporal position of the knot points is set relative to the adjacent R waves, using an operator assisted designation of the t-p interval. The voltage values used for the knot points are obtained by linear regression of the designated t-p interval, which enables significantly better noise rejection and utilizes the fact that the baseline itself should be "flat", i.e. linear.

Pulse Histogram View

It is difficult to provide a visual representation of a long and complicated time series such as an ECG. Prior art suggests the use of spectrograms, but these are hard for doctors to interpret, as are autocorrelations and other staple tools of the art of signal processing. That is to say a doctor has undergone training in recognizing ECGs and the features of the heartbeat using the standard representation. A new representation that requires the doctor to learn ECG recognition anew is likely to meet resistance to its introduction.

By contrast, the pulse histogram view of the current embodiments provides a representation of the ECG that is intuitive to interpret, particularly for a doctor with standard training. The color of a pixel at some voltage and offset from the R-wave encodes the log-likelihood of finding that voltage at that offset from the R-ware peak. As an additional aid, the mean and standard deviations are preferably plotted on top of the histogram, as in fact illustrated in FIG. 3. Since the standard deviation itself conflates temporal variation with electrical variation in those regions where there is electrical change, a further renormalized variance indicator is preferably plotted on the same graph, and examples are indicated in the ECG visualization examples hereinbelow.

The histogram, provided for example as a bitmap file, is deceptively simple. The histogram looks like a plot of a single "time averaged" beat with some blurry colors. In fact it encodes the statistical distribution of the ECG during all beats, and enables the electrocardiologist to tell at a glance what sort of distribution governs each portion of the beat.

For example, a patient with an intermittent "p-mitrale" symptom (a "dip" in the peak of the p wave) would be difficult to spot by looking at the standard ECG. It would also be difficult to spot on a time average plot because the intermittent nature of anomaly would be averaged out over time. However, it would show clearly on the pulse histogram as a branching near the peak of the p wave.

Beat to Beat Plot

The R-R intervals play an important role in the ECG, as they represent the overall rhythm of the heart and are used for diagnosing arrhythmias. We plot the R-R interval at the time of the first R wave. By visually associating the R-R interval with its time of occurrence, we make it easier to spot rhythm anomalies in the plot of the ECG signal itself.

Using the Beat to Beat plot, it is possible to quickly zoom in on symptoms such as escape beats within an ECG that is minutes (i.e. hundreds of beats) long. The beat to beat plot referred to here is a conventional ECG plot enhanced with baseline estimates as described herein and using oversampling.

Vector Plot

The vector plot represents the changing direction of the heart's depolarization over each beat, as resolved by using multiple leads. By encoding the time axis as change in color, the Vector Plot enables the doctor to see at a glance whether the time evolution of the depolarization follows a normal pattern. Encoding multiple leads into the Vector Plot provides an additional benefit—it enables the doctor to rotate the vectors in an intuitive way, thereby presenting a reconstructed virtual ECG signal from any selected direction. Without the Vector Plot, the natural variability in heart orientation causes ECG signals of different people to appear less similar than they may really be.

Figure 9:
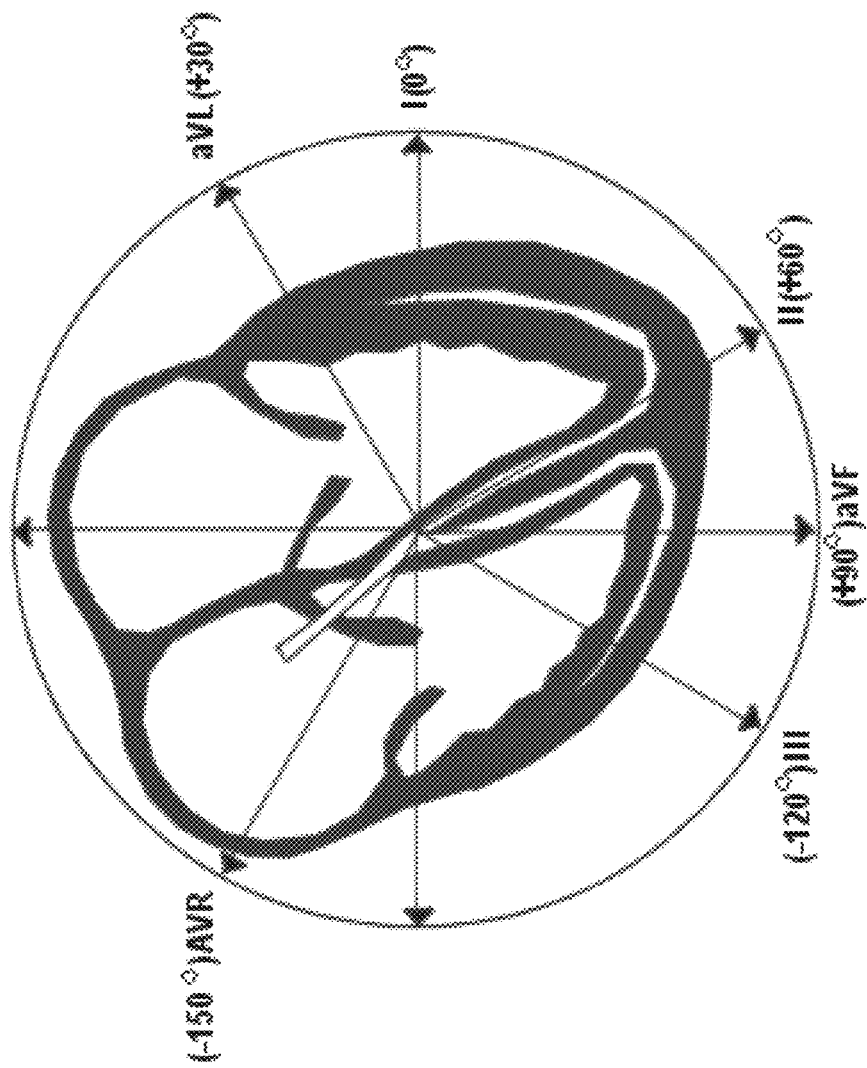

As shown in FIG. 9, the normal orientation of the heart is such that each ECG lead resolves a different spatial component of the electrical activity (see diagram below). If the heart is rotated relative to the normal orientation, even perfectly normal electrical activity will look significantly different, because the same components are measured from a rotated pattern of activity.

Figure 10:
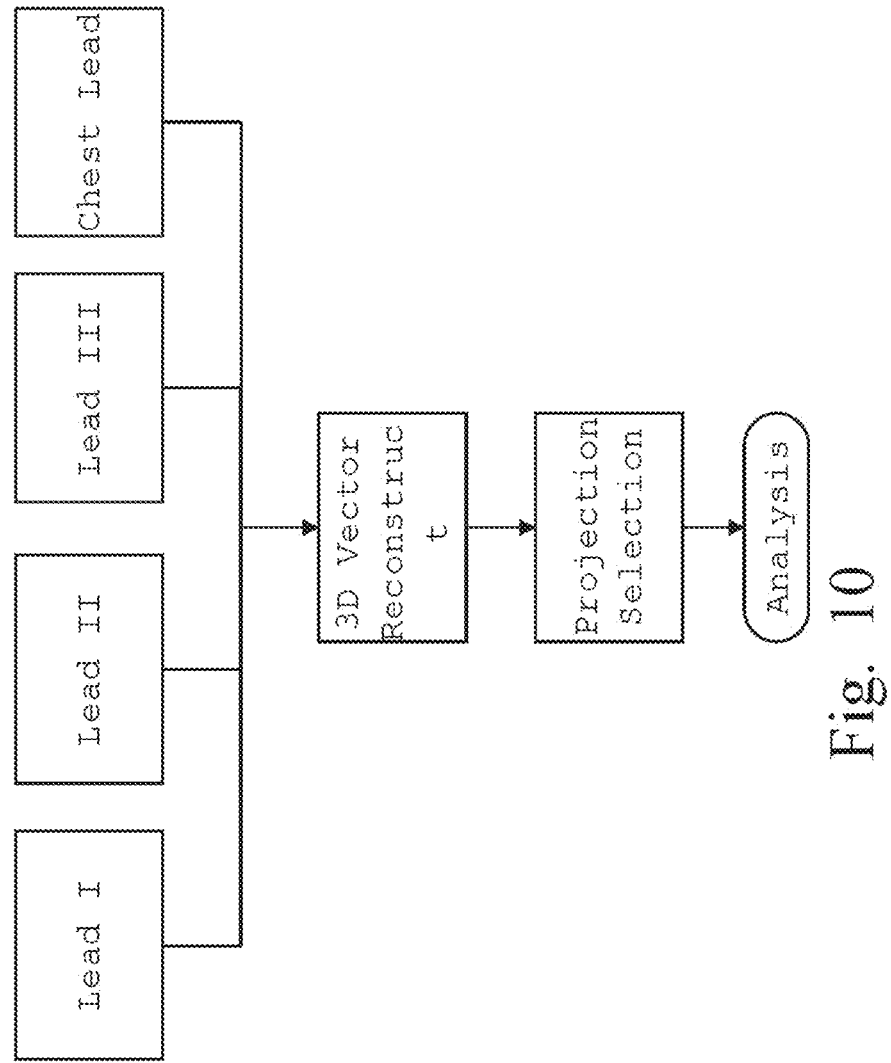

The vector based ECG analysis is performed using a process described with reference to FIG. 9 which shows a series of linear projections over the heart representing the view so to speak presented to different leads. Each projection derived from the vector analysis may be subjected to the same analysis process as described above for ECG signals. The leads may be connected together as shown in FIG. 10 to give a three-dimensional vector analysis and thereby provide the vector plot.

An advantage of the vector plot is the ability to convert signals between leads, which is to say to show what the signal would be if the heart were at a different angle. Thus the plot succeeds in removing much of the variation between patients Aligned and Unaligned Recurrence Plots The use of Recurrence Plots, with and without timing corrections for beat times, provides a valuable alternative to the use of spectrograms, autocorrelation plots and lag-plot embeddings that are the more common tools in use by the signal processing community.

Here the advantage is the obvious two dimensional nature of the Recurrence Plot, which makes it much easier for doctors to interpret.

ECG Scanning Device

Figure 11:
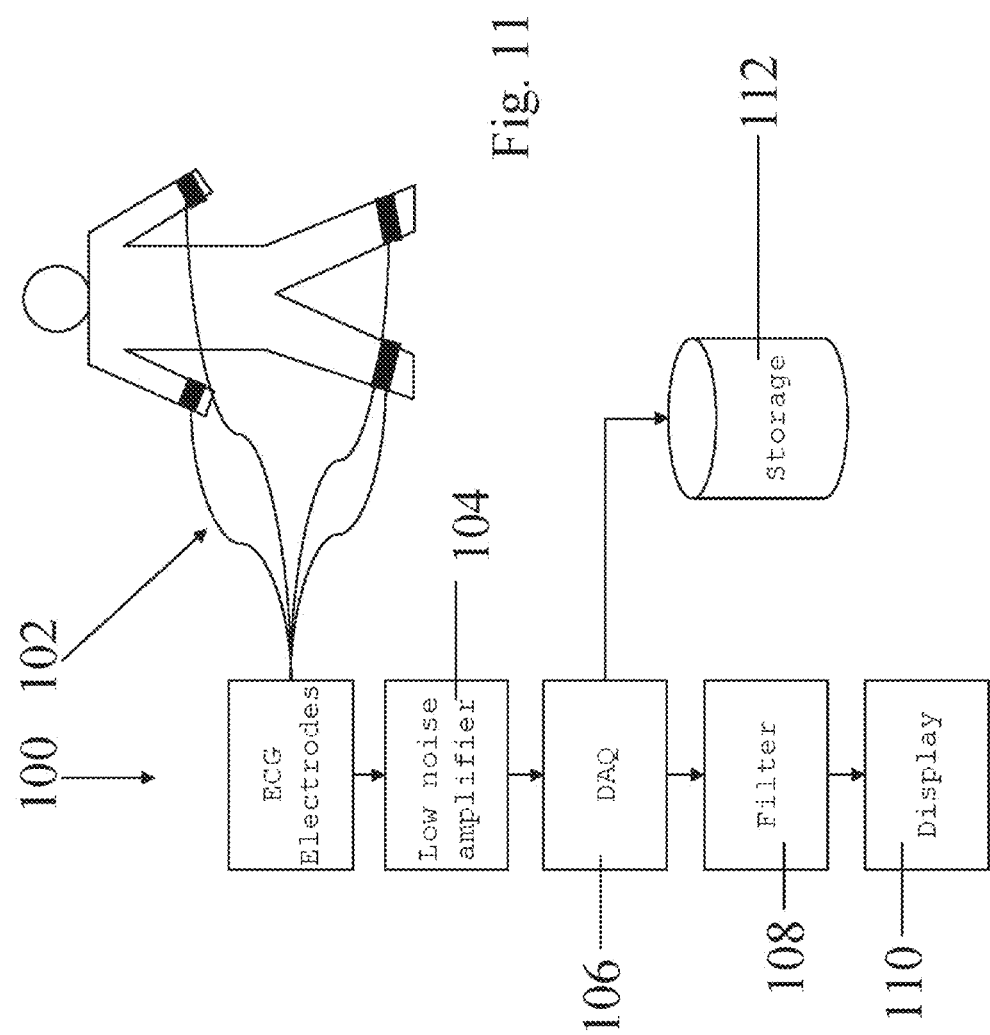

Reference is now made to FIG. 11, which is a simplified block diagram that illustrates the structure of a preferred embodiment of an ECG scanner device according to the present invention.

The scanner 100 requires multiple leads 102 to be attached to the patient. These leads are connected to a LNA (low noise amplifier) 104 with a high CMRR (common mode rejection ratio) and a large dynamic range. These properties are necessary in order to prevent the measurement from saturating. Sometimes the LNA is available as part of a data acquisition device, but more often one must build an analog LNA and use it with a simpler data acquisition device DAQ 106.

The scanner records the raw samples provided by the DAQ 106 for transmission and subsequent analysis.

Additionally, the samples are passed through a digital bandpass filter 108 and the filtered result is displayed in real time on display unit 110. This signal shown is similar to the approximate signal above. The display aids the doctor/nurse in adjusting the ECG leads correctly.

Reference is now made to FIG. 12, which shows the process of FIG. 6 together with the further features discussed later on in the application.

Reference is now made to FIG. 13, which is a simplified diagram illustrating a construction of the system of the present invention for remote analysis. A scanner unit 110 may be located at a first location. A storage and logic unit may be located at a second location and remote monitoring unit 114 may be located at a third location. Each such remote monitoring unit may be conveniently located for an experienced cardiologist.

Reference is now made to FIGS. 14-39, which are a series of ECG representations showing six case studies in each of which a standard ECG plot is compared with a plot according to a preferred embodiment of the present invention. The conventional ECG plots in each case indicate a normal ECG pattern. In all six cases the patients have undergone coronary angiography ("heart catheterization")

Figure 14:
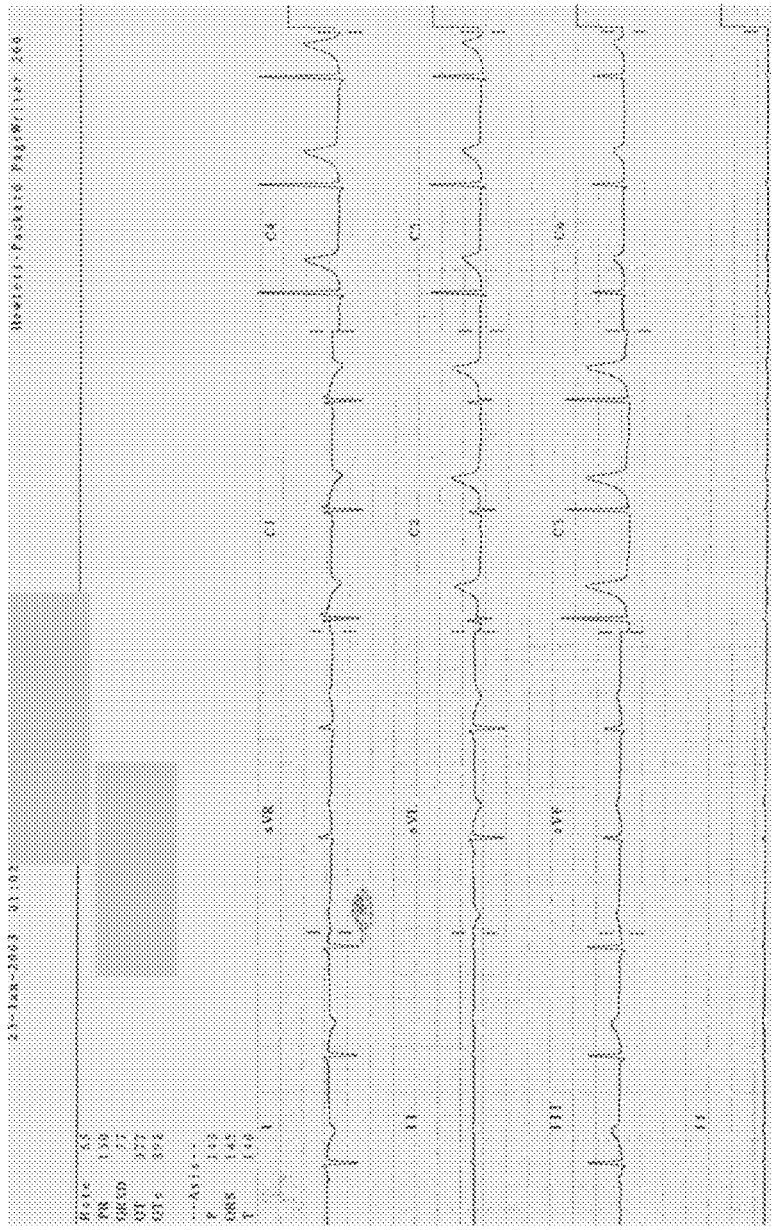
Figure 15:
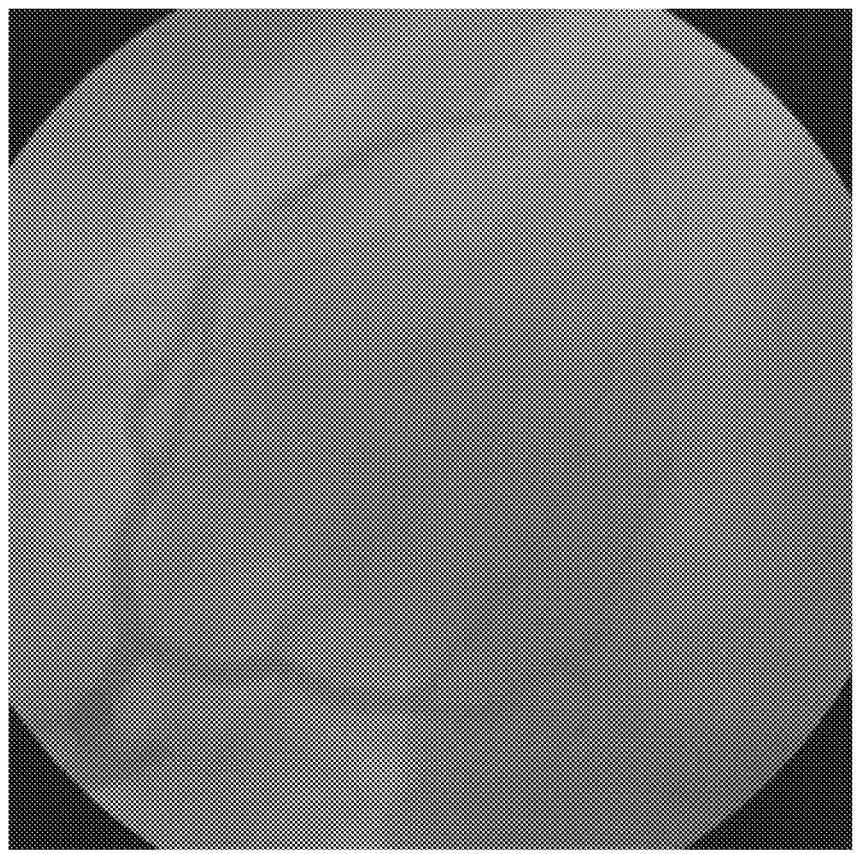
Figure 16:
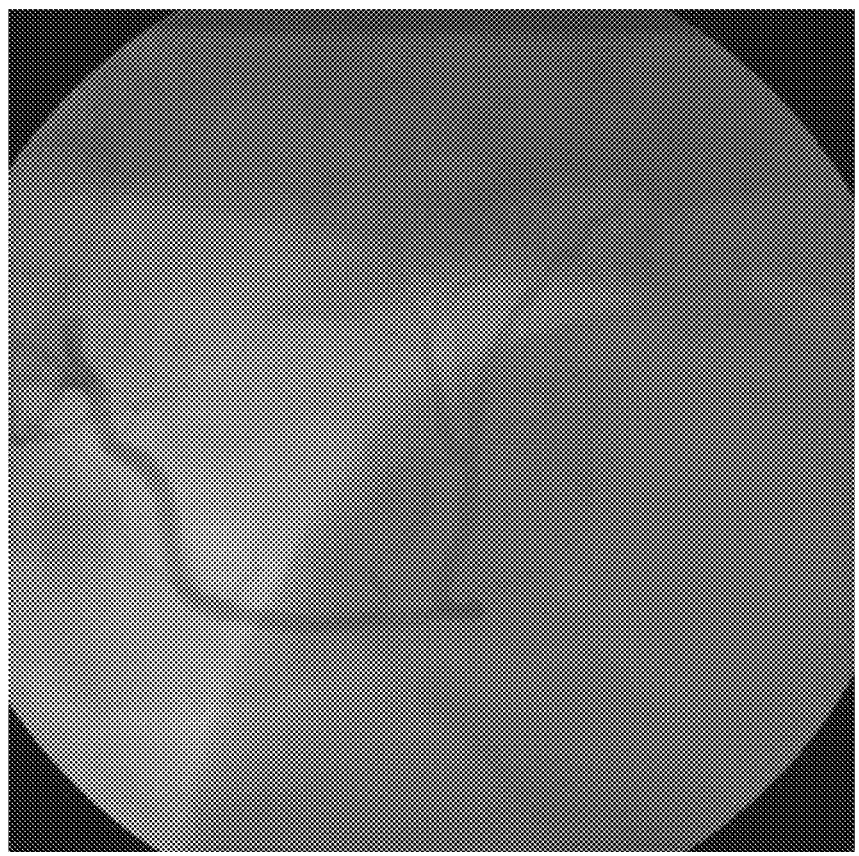
Figure 17:
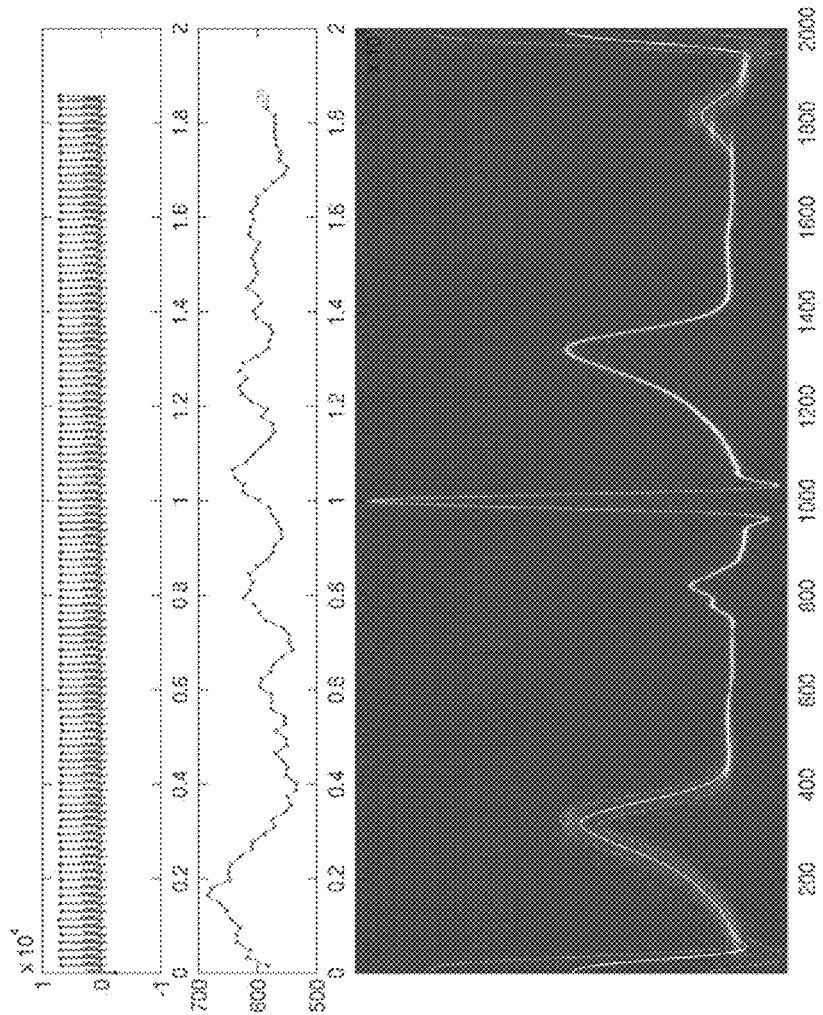

FIGS. 14 to 17 show a first case study. In this first study FIG. 14 shows a conventional 12 leads ECG records that was diagnosed as normal by two cardiologists. FIGS. 15 and 16 illustrate the left and right coronary arteries of the same patient respectively and these have a normal anatomy with no atherosclerotic disease. FIG. 17 shows a visualization of the ECG signal according to embodiments of the present invention as described above. The visualization shows that all the ECG complexes falls into the same region to give a narrow looking pattern indicates almost no variability of the various segment throughout the ECG cycles. This lack of variability is in significant correlation with the underlying normal anatomy of the coronary arteries.

Figure 18:
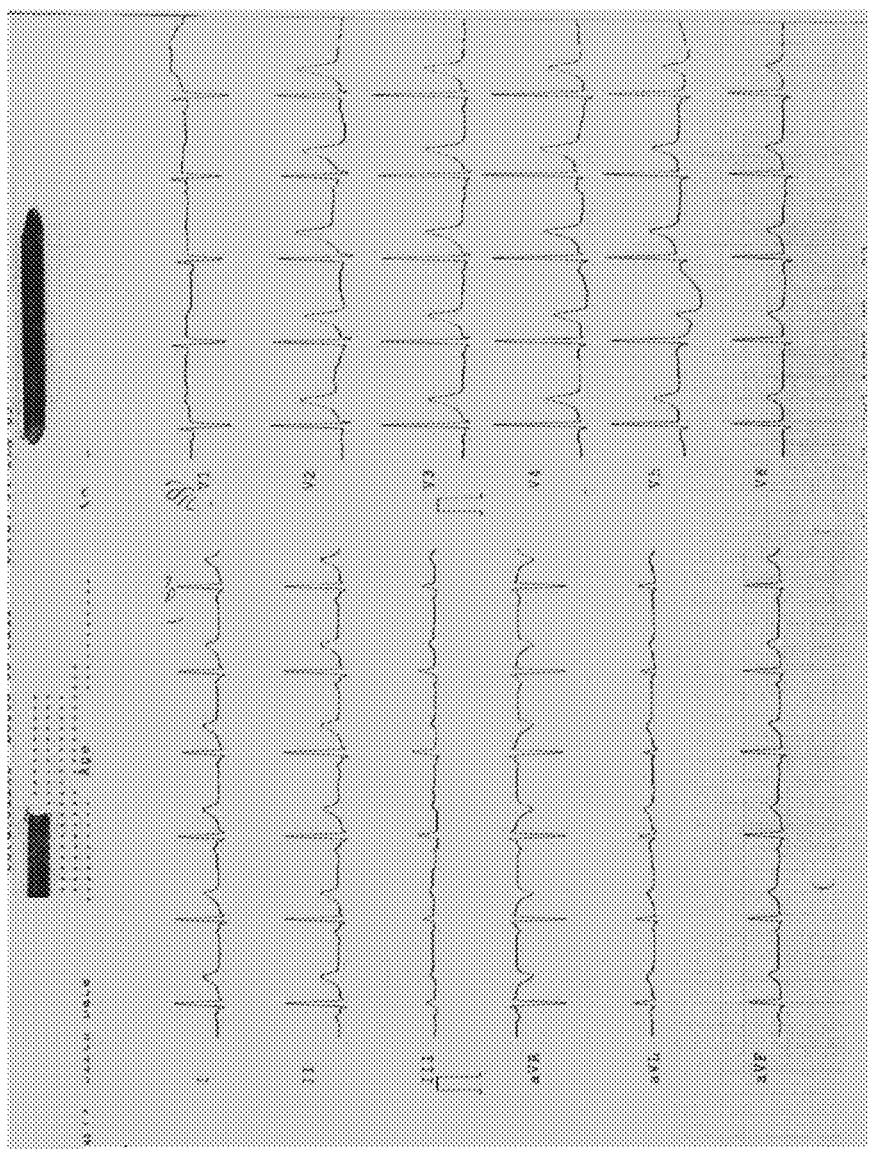
Figure 19:
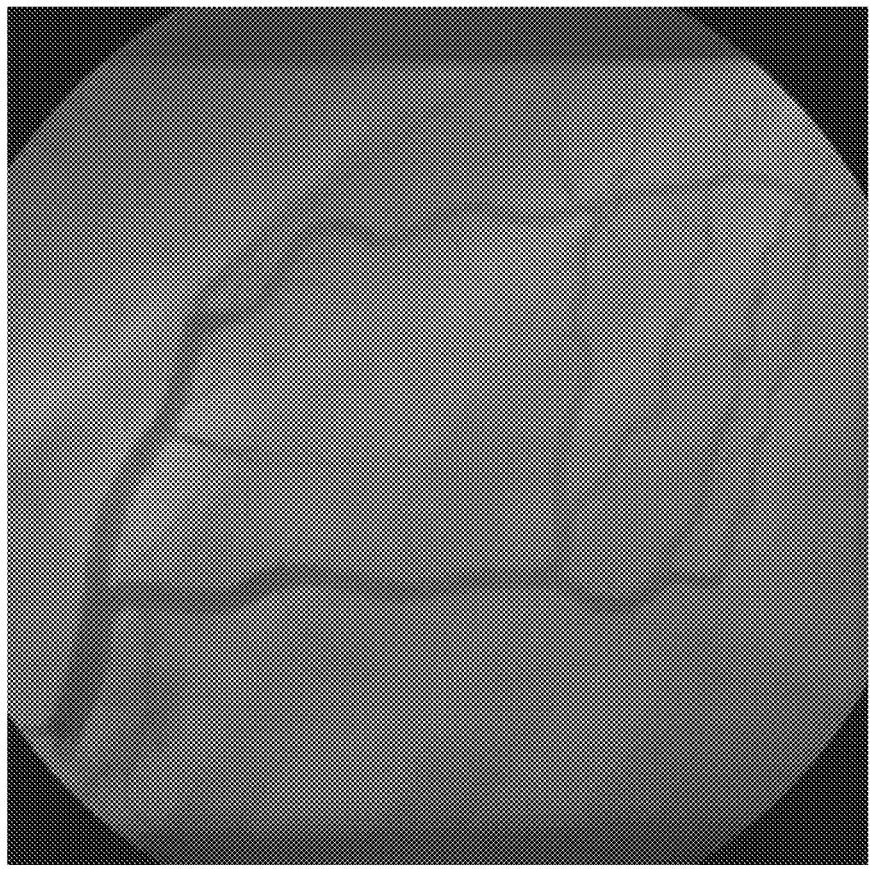
Figure 20:
Figure 21:
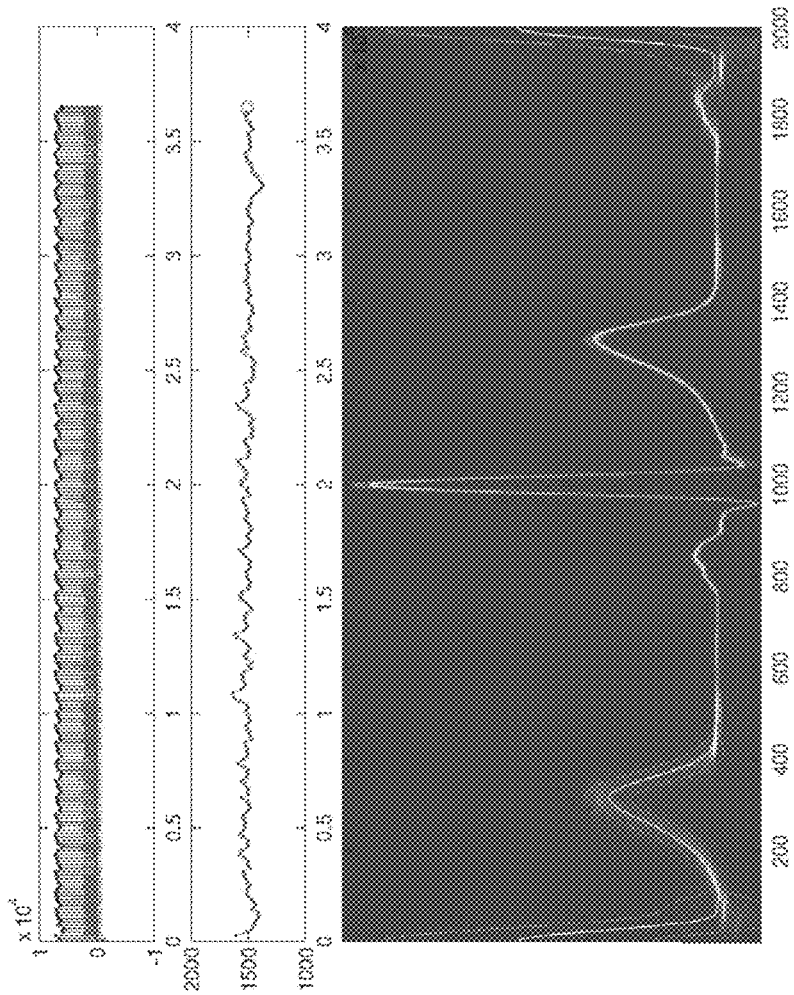

FIGS. 18 to 21 indicate a second case study. FIG. 18 shows an apparently normal conventional ECG readout. FIGS. 19 and 20 show normal left and right coronary arteries of the same patient and FIG. 21 shows the typical narrow pattern created by present invention, indicates lack of variability that correlates with the underlying normal coronary arteries very similar to the visualization shown in FIG. 17.

Figure 22:
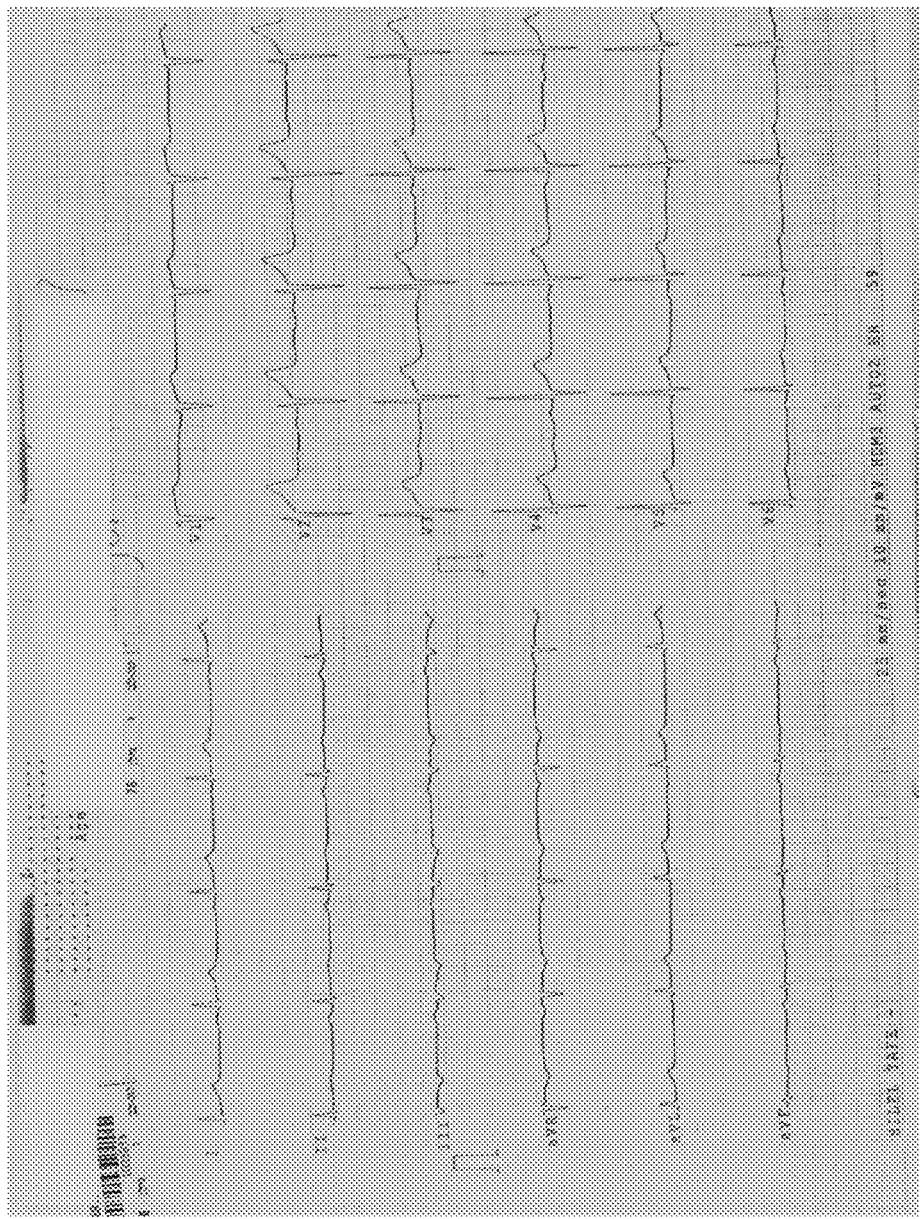
Figure 23:
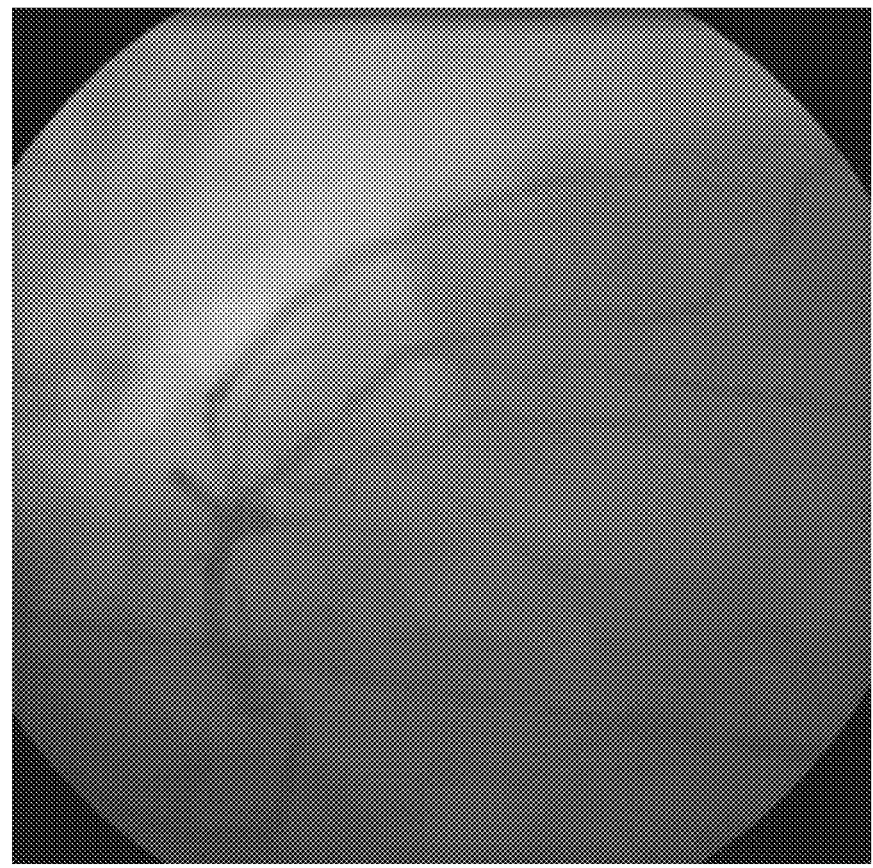
Figure 24:
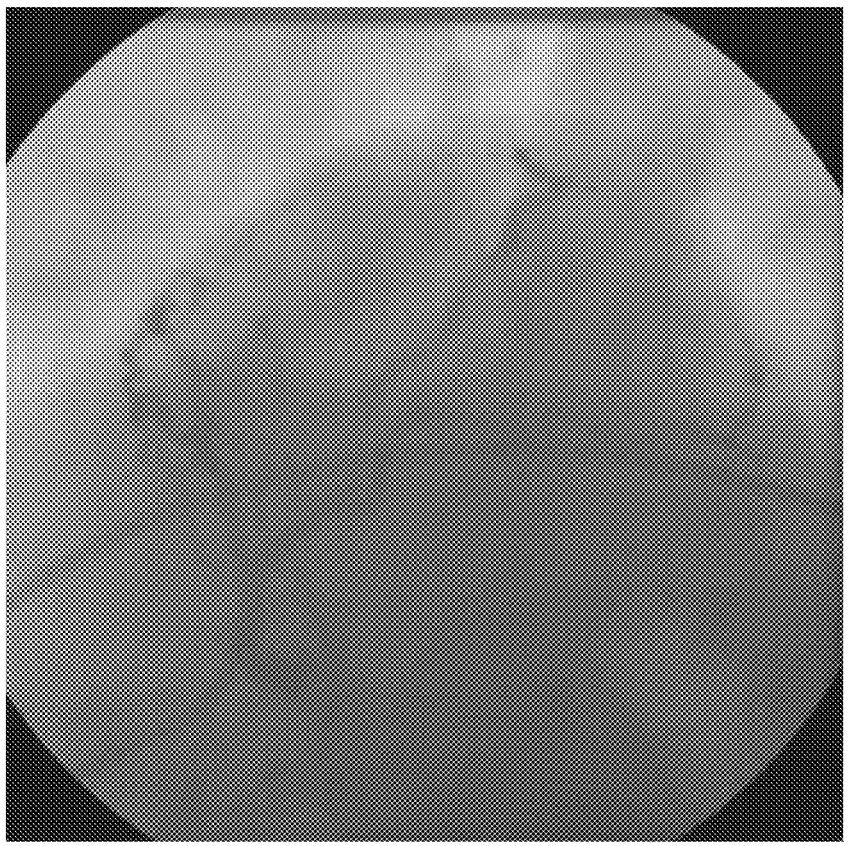
Figure 25:
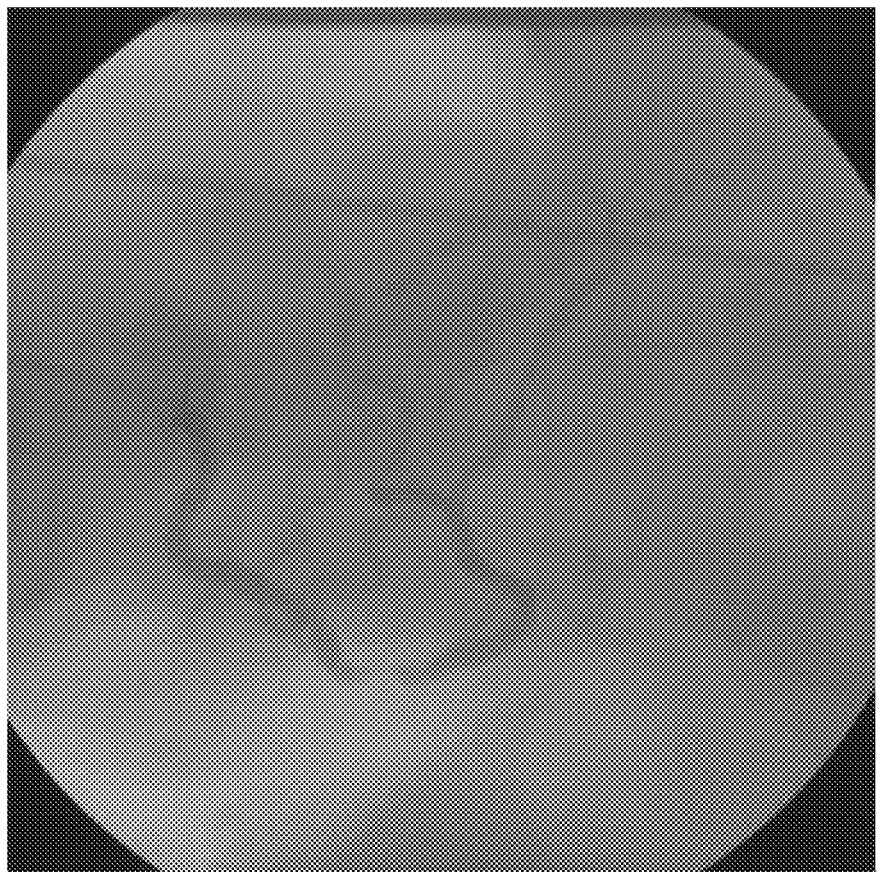
Figure 26:
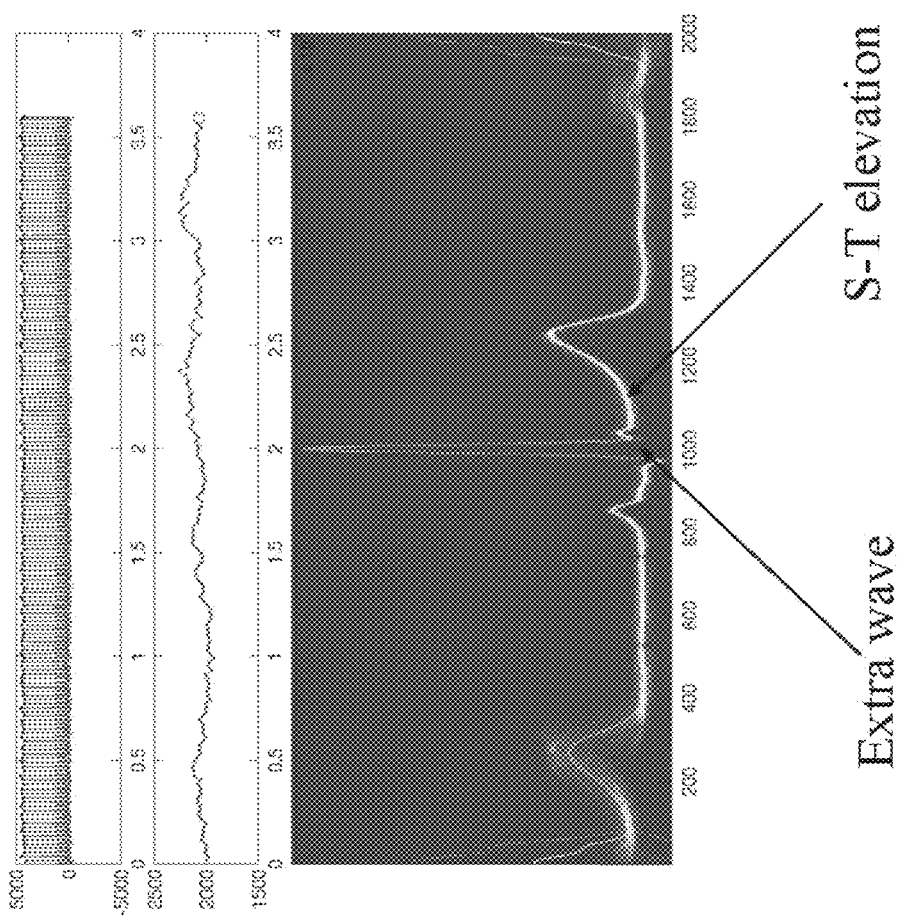
Figure 27:
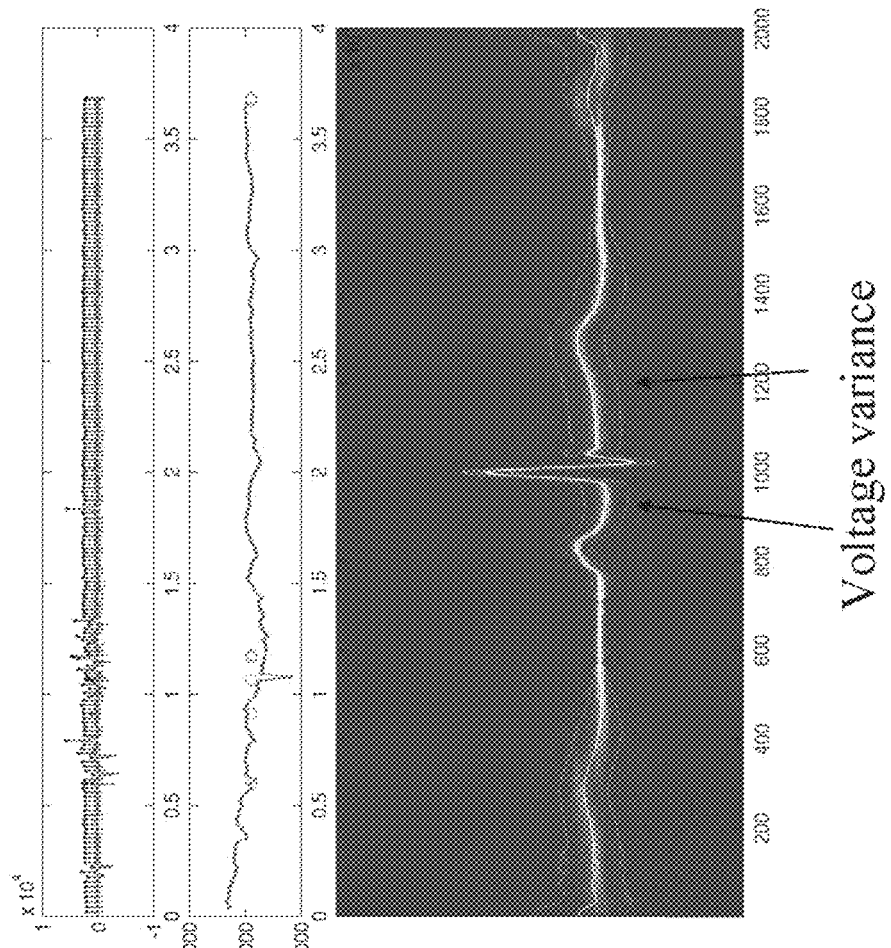

FIGS. 22 to 27 show a third case study. FIG. 22 illustrates another apparently normal conventional ECG. FIGS. 23, 24 and 25 however show diseased coronary arteries of the same patient. Two views are shown of the left artery so as better to show the pathology. FIG. 26 shows the ECG visualization according to the present embodiments, taken from lead 1, and in this case two abnormalities are apparent. One is an extra wave just after the QRS complex and the other is an ST elevation. Neither of these features are apparent from the conventional ECG. FIG. 27 shows visualization according to the present embodiments using lead 2. As well as the additional features referred to above, a large spread of the voltage amplitude can be seen at both sides of the big R wave. This phenomenon of voltage variance (indicated by the two arrows) can be seen only by using the embodiments of the present invention as described above, and it is in significant correlation with the underlying diseased coronary arteries.

Figure 28:
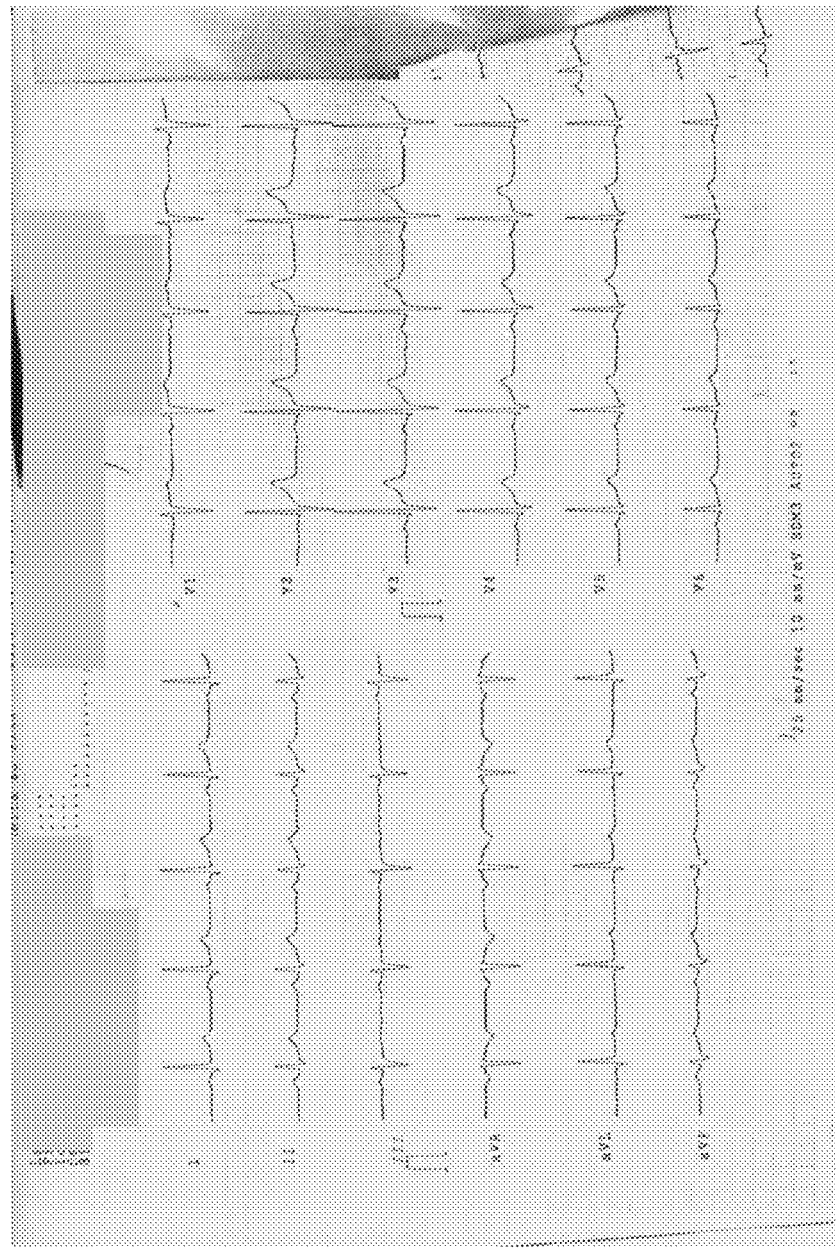
Figure 29:
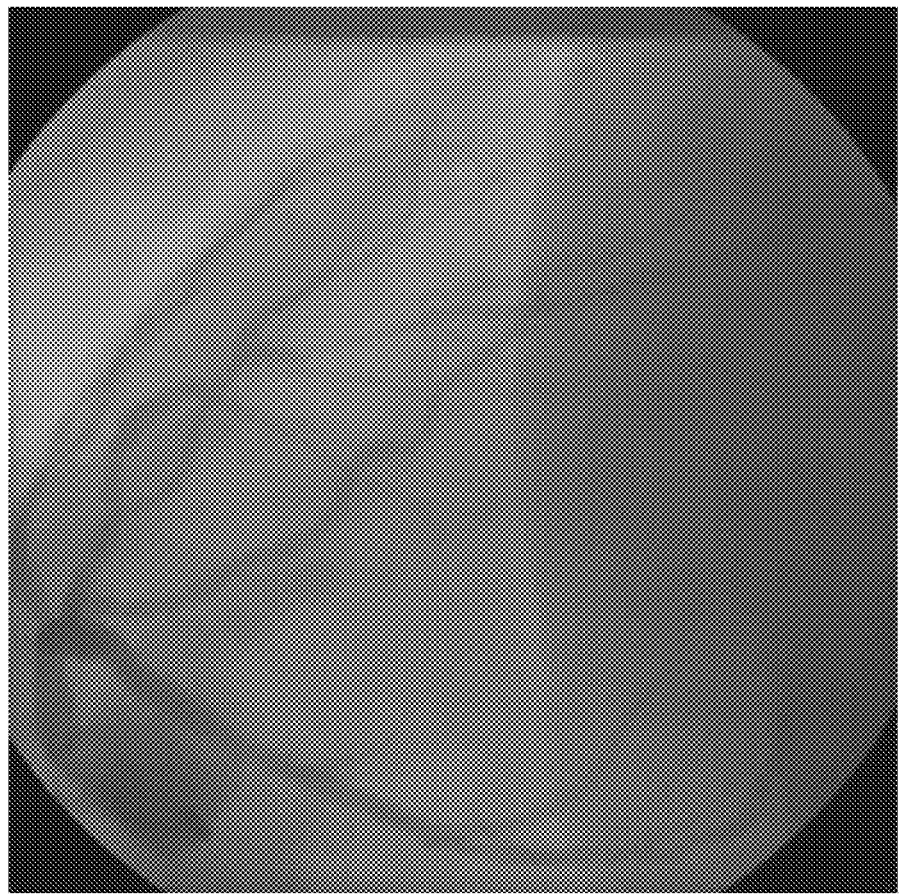
Figure 30:
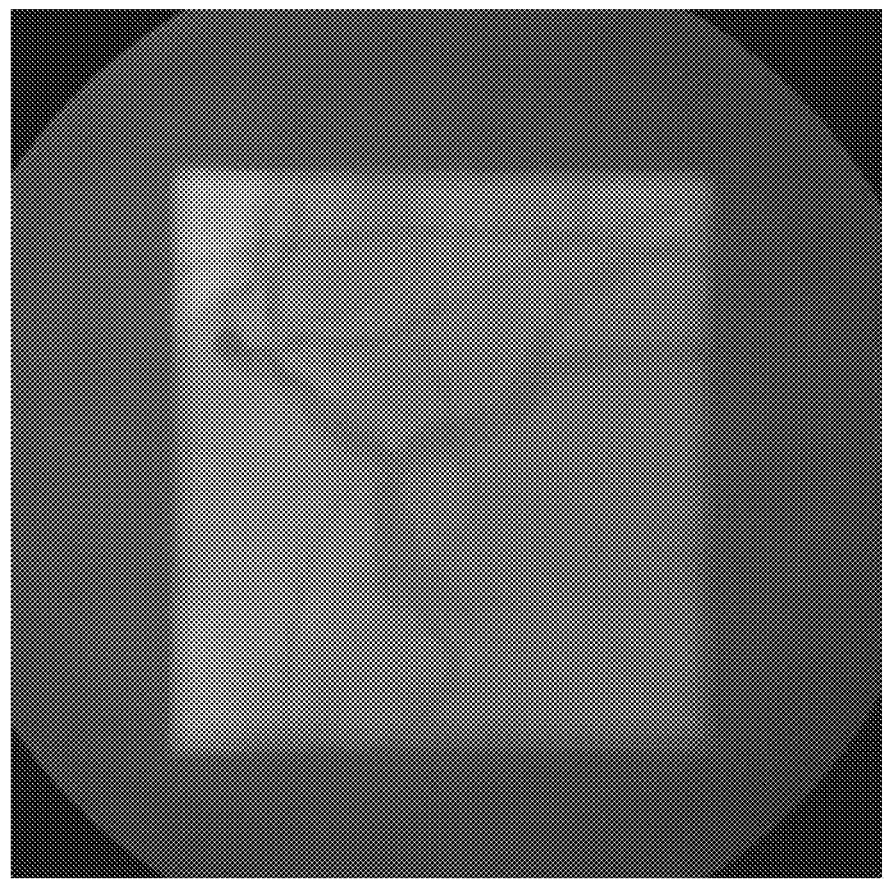
Figure 31:
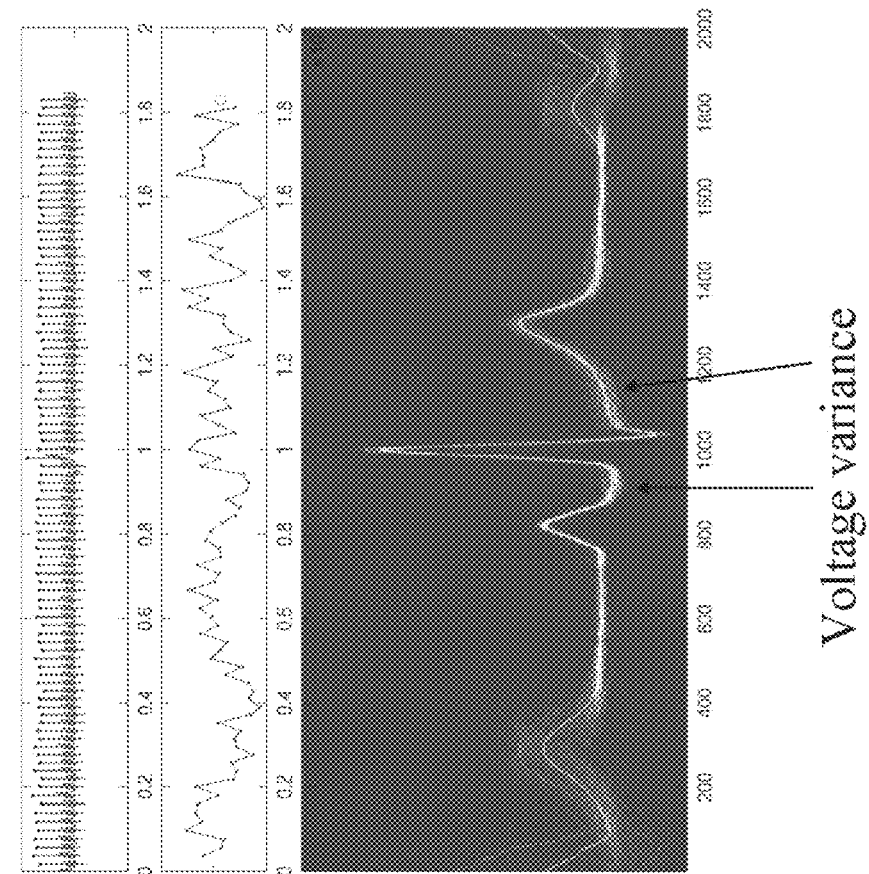

FIGS. 28 to 31 show a fourth case study. FIG. 28 illustrates another apparently normal conventional ECG pattern. FIGS. 29 and 30 however show diseased coronary arteries of the same patient. More specifically FIG. 29 shows the left dominate coronary artery with diffuse disease that narrows its lumen. and FIG. 30 shows narrowing in the left main artery. FIG. 31 shows the ECG visualization according to the present embodiments, and in this case a large voltage variance is shown at both sides of the big R wave again indicating coronary artery disease.

Figure 32:
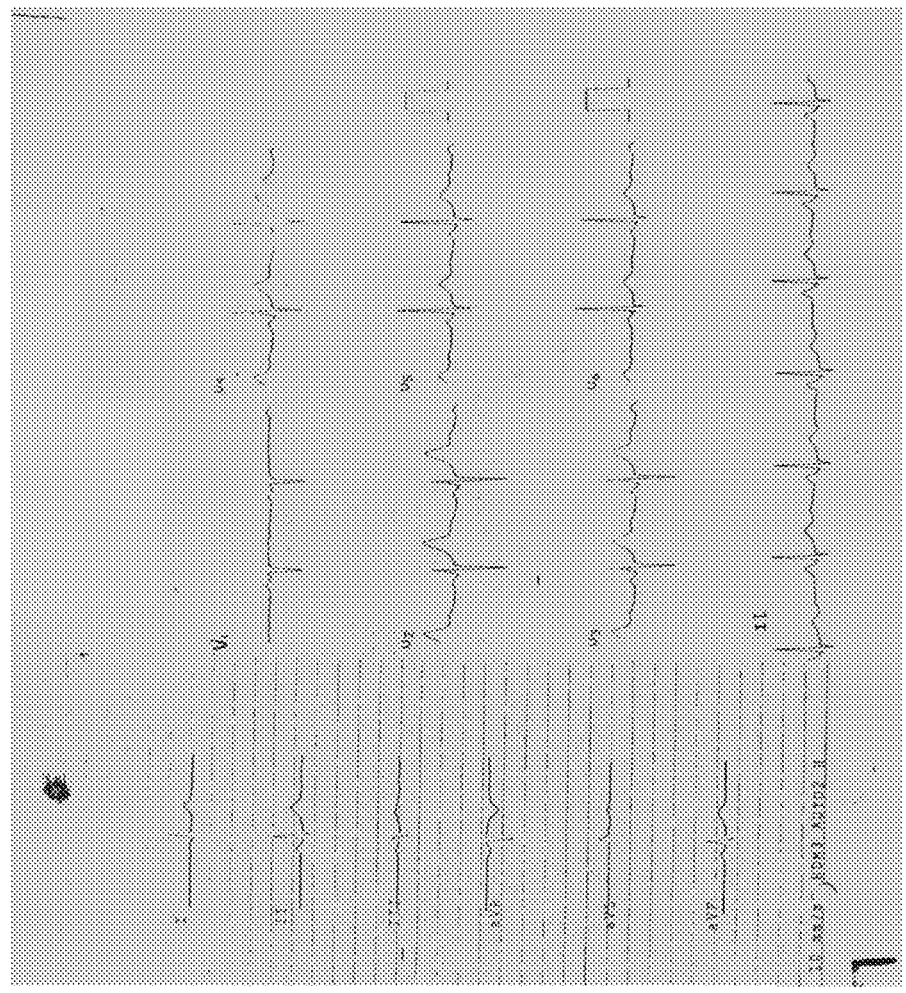
Figure 33:
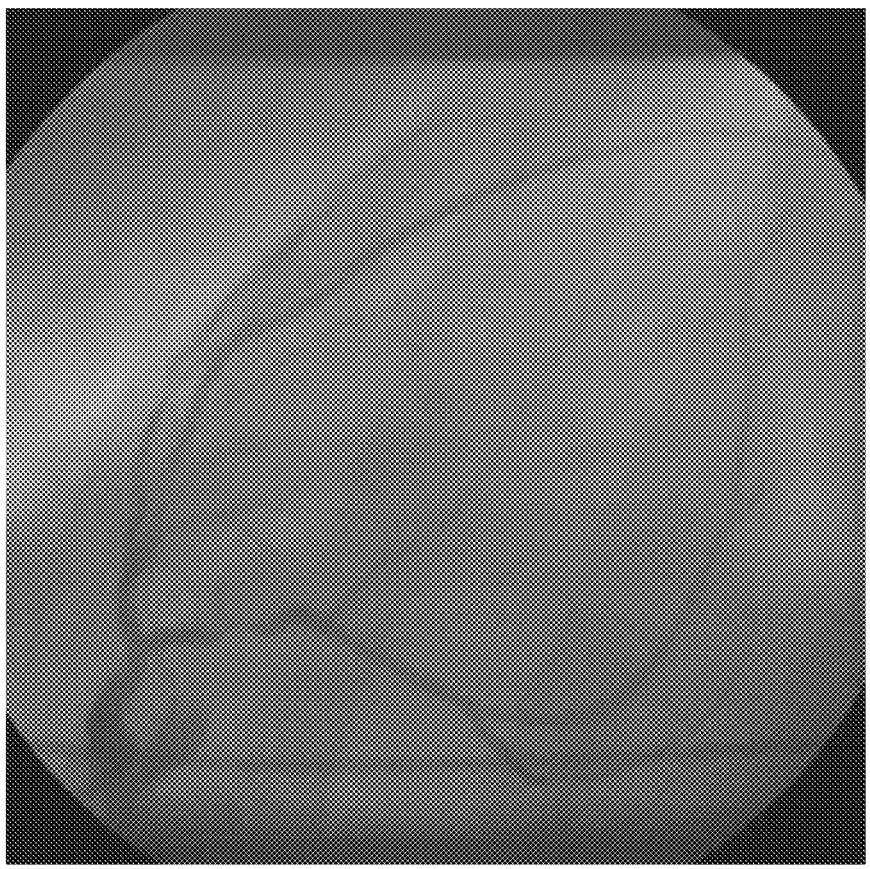
Figure 34:
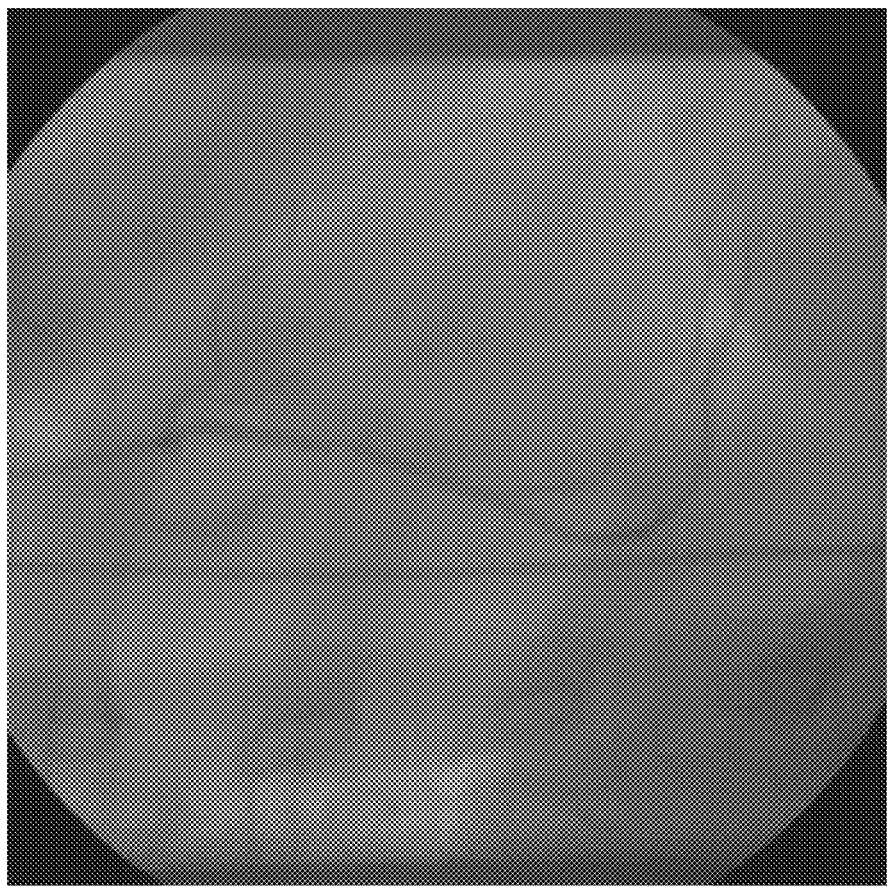
Figure 35:
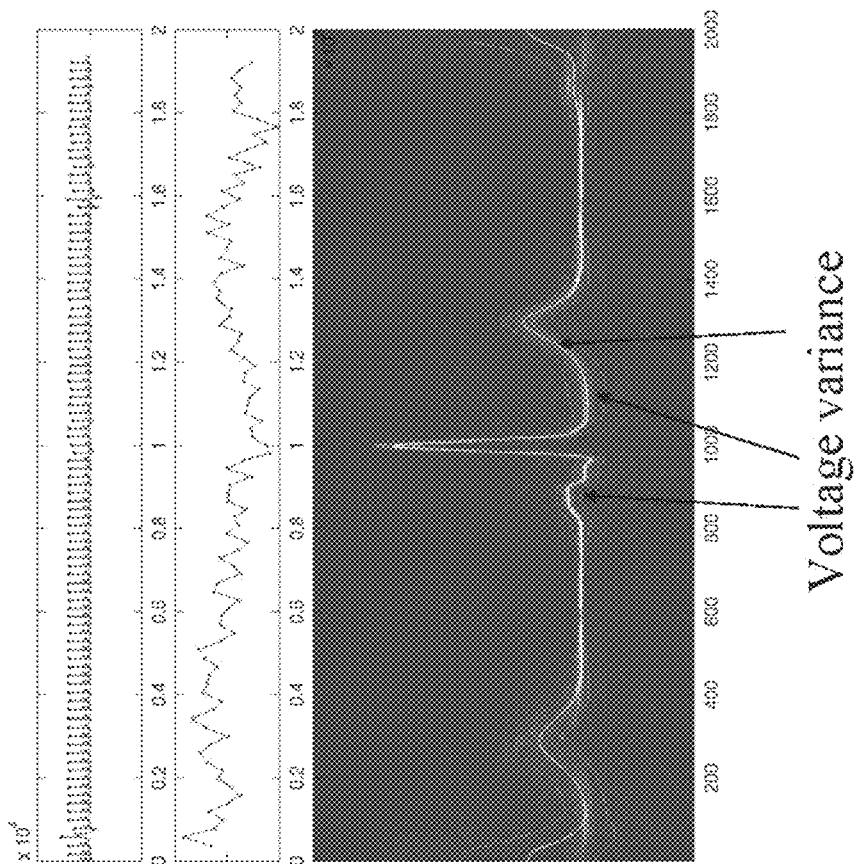

FIGS. 32 to 35 show a fifth case study. FIG. 32 illustrates another apparently normal conventional ECG. FIGS. 33 and 34 however show diseased left and right coronary arteries of the same patient respectively. FIG. 35 shows the ECG visualization according to the present embodiments, and in this case again a large voltage variance is apparent over the complex again indicating coronary artery disease.

Figure 36:
Figure 37:
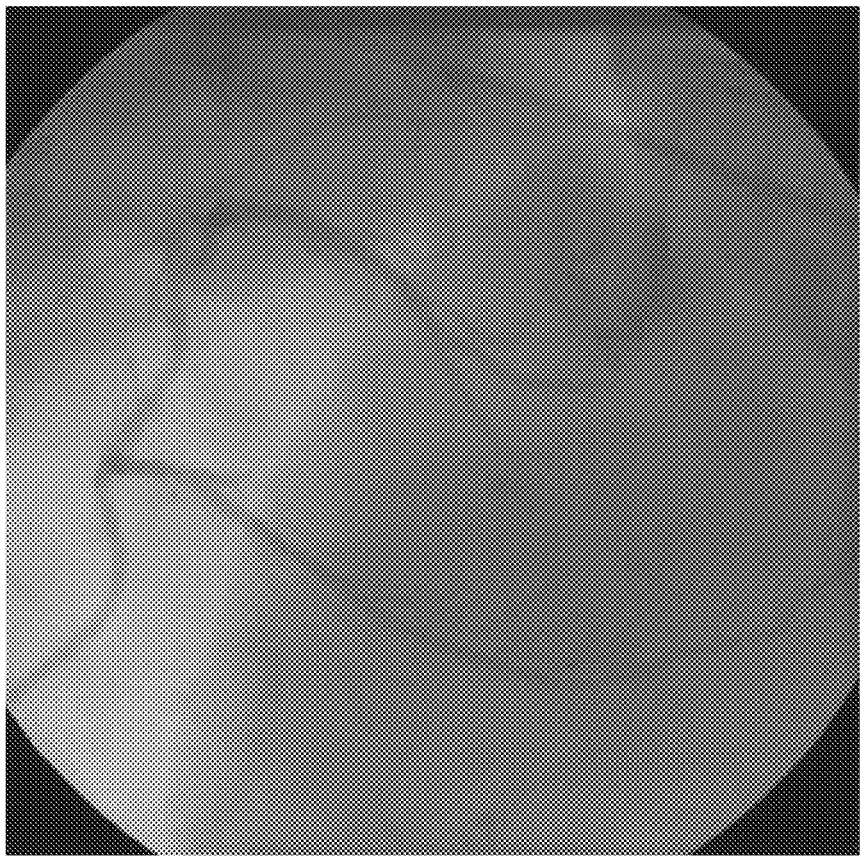
Figure 38:
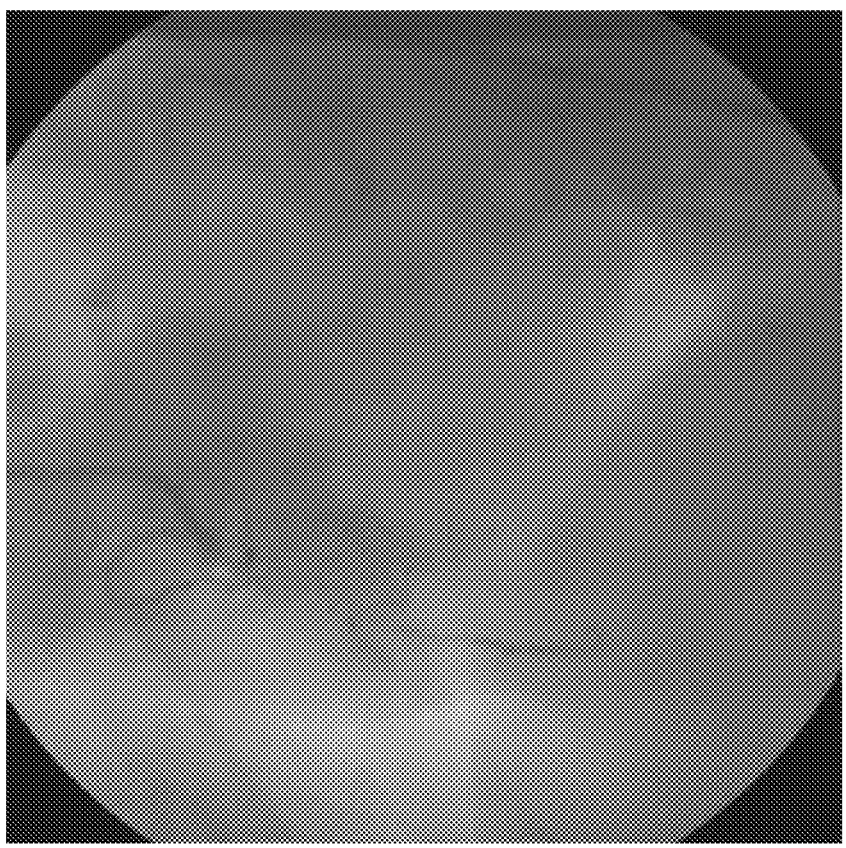
Figure 39:
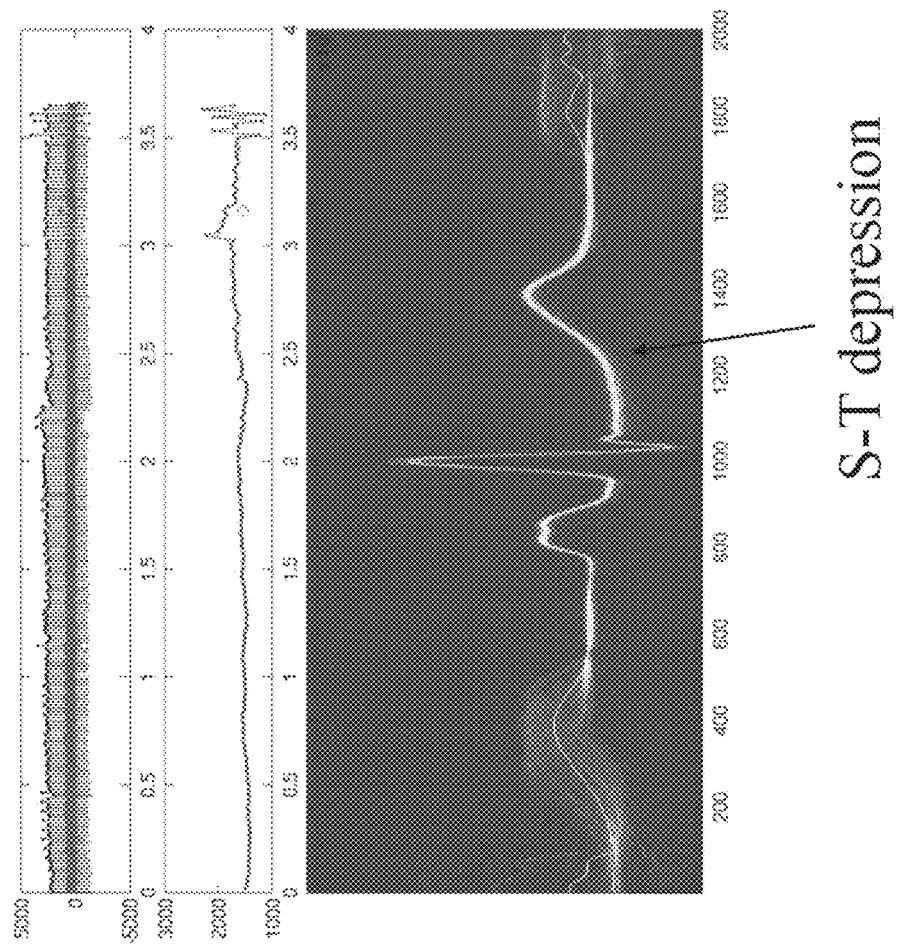

FIGS. 36 to 39 show a sixth case study. FIG. 36 illustrates another apparently normal conventional ECG. FIGS. 37 and 38 however show diseased coronary arteries. Specifically FIG. 37 shows the left coronary artery exhibiting LM ostial stenosis. FIG. 38 shows the diseased right artery. FIG. 39 shows the ECG visualization according to the present embodiments, and in this case two abnormalities are apparent, the same voltage variance as before and an ST depression can clearly be seen. The feature is not apparent from the conventional ECG.

Reference is now made to FIG. 40 which shows part of an ECG scan according to a preferred embodiment of the present invention and illustrates how color coding is useful in making variance in the signal immediately evident to the practitioner. Color separation is here used to distinguish between short beat (short R-R) shown in yellow and indicated by reference numeral 180, and long beat shown in blue and indicated by reference numeral 182. The R-R plot 184 above also shows instability in the lengths of heartbeats and the color separation simply sets a threshold between short and long beats and applies different colors above and below the threshold. Clearly two different shapes appear in the P wave and the color coding clearly shows that the two shapes belong quite neatly to the different color codes. Without coloring it would not be apparent that the peaked P wave appears after and is explicitly associated with short beats and that the normal P wave appears only after longer beats.

Furthermore it is apparent that there is a slight S-T depression 186 associated with the short beat. All of these details are important clinically.

Reference is now made to FIG. 41 which also shows part of an ECG scan, and here illustrates the value of including the R-R time plot together with the combined plot. Looking at R-R 188 plot it is clear that something abnormal occurs between times 2 and 2.5. The R-R plot can then be used to zoom in on the actual heartbeats in the compressed complete data 190 that occur at that time, and the cause is found to be two abnormal beats.

Reference is now made to FIG. 42, which illustrates a control screen 200 for multi-lead sampling according to a preferred embodiment of the present invention. Multi-lead sampling takes data from the different leads, which represent the heart signal from different directions. A combined plot is then possible based on any desired direction and FIG. 42 illustrates an arrow 202 superimposed over an anterior view of the heart 204. Dial 206 is used to allow the arrow to be set for any angle about the heart so that a plot can be produced for the desired direction.

FIG. 43 shows the same anterior view with arrow 202 placed in a different direction.

FIG. 44 shows control screen 200, this time with a lateral view 208 of the heart.

FIG. 45 shows control screen 200, and indicates a posterior view 210 of the heart.

It is expected that during the life of this patent many relevant scanning and signal processing devices and systems will be developed and the scope of corresponding terms herein is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method for graphical representation of a train of ECG complexes, each of said electrocardiogram (ECG), complexes respectively comprising an R wave and a T-P interval and having respectively variable isoelectric baselines, the method implemented on an electronic processor, the method comprising:
    obtaining electrocardiogram (ECG) signals from electrodes placed on a subject and, using said electronic processor, carrying out two alignments for each complex as follows:
    aligning said complexes in terms of signal amplitude by obtaining a respective T-P interval for each ECG complex, using said T-P interval to infer said respective isoelectric baseline and aligning said isoelectric baselines; and
    aligning said complexes temporally using a predetermined point on respective R-waves, thereby to graphically represent said train of ECG complexes as a superposition of said ECG complexes into a single complex.

2. The method of claim 1, comprising obtaining said train separately from each one of a plurality of leads at different locations on a subject.

3. The method of claim 2, comprising processing said train as obtained from said different leads as a linear projection of said train in a direction to a respective lead from the heart, thereby to provide a three-dimensional vector plot of said train.

4. The method of claim 1, comprising obtaining said train of ECG complexes using a sampling rate in excess of 1 KHz.

5. The method of claim 1, comprising obtaining said train of ECG complexes as at least a sixteen bit signal.

6. The method of claim 1, comprising carrying out said aligning of said isoelectric baselines using respective T-P intervals by use of polynomial cubic hermite splines.

7. A method of electronically displaying electrocardiogram (ECG) representations of respective heartbeats of a patient comprising:
    obtaining ECG complexes as respective signals of succeeding heartbeats from a patient, said obtaining using electrodes placed on said patient,
    electronically aligning said ECG signals by obtaining a respective T-P interval for each ECG complex, using said T-P interval to infer said respective isoelectric baseline and aligning said isoelectric baselines, and aligning said complexes temporally using a predetermined point on respective R-waves,
    superimposing said aligned complexes into a single complex, and electronically displaying said single complex, thereby to provide a representation of variations in an ECG signal over time.

8. The method of claim 7, wherein said superimposing comprises retaining shape information of said ECG representations so that said displaying said superimposed signals comprises displaying shape variation of said ECG signals.

* * * * *